United States Patent
Whaley et al.

[19]

[11] Patent Number: 6,119,688
[45] Date of Patent: Sep. 19, 2000

[54] POWDER DISPENSER

[75] Inventors: Ralph Duane Whaley, Roseville; Mark Steven Shinnick, White Bear Township, Ramsey County; Charles G. Thiel, St. Paul, all of Minn.; DonGene Kriegl, Hudson, Wis.; Thomas Ward Reeder, St. Paul, Minn.; Brian Mark Pattock, Circle Pines, Minn.; Robert John Mattila, Mahtomedi, Minn.; Thomas Anthony Turgeon, Fridley, Minn.

[73] Assignee: 3M Innovative Properties Company, St. Paul, Minn.

[21] Appl. No.: 08/456,850

[22] Filed: Jun. 1, 1995

Related U.S. Application Data

[63] Continuation of application No. 07/975,625, Nov. 12, 1992, abandoned, which is a continuation-in-part of application No. 07/817,331, Jan. 6, 1992, abandoned, which is a continuation-in-part of application No. 07/749,912, Aug. 26, 1991, abandoned.

[51] Int. Cl.[7] .................................................. A61M 15/00
[52] U.S. Cl. ............................. 128/203.15; 128/203.21; 128/203.12
[58] Field of Search .................... 128/203.12–203.23, 128/200.14, 200.16; 604/56, 58

[56] References Cited

U.S. PATENT DOCUMENTS

| | | |
|---|---|---|
| 3,157,179 | 11/1964 | Paullus et al. . |
| 3,187,748 | 6/1965 | Mitchell et al. . |

(List continued on next page.)

FOREIGN PATENT DOCUMENTS

| | | |
|---|---|---|
| 0 232 235 | 8/1987 | European Pat. Off. . |
| 0 407 028 | 1/1991 | European Pat. Off. . |
| 0 424 790 A2 | 5/1991 | European Pat. Off. . |
| 0 441 643 | 8/1991 | European Pat. Off. . |
| 0 467 172 | 1/1992 | European Pat. Off. . |
| 0 469 814 | 2/1992 | European Pat. Off. . |
| 0 488 609 | 6/1992 | European Pat. Off. . |
| 0 490 797 | 6/1992 | European Pat. Off. . |
| 0 505 321 | 9/1992 | European Pat. Off. . |
| 0 520 440 | 12/1992 | European Pat. Off. . |

(List continued on next page.)

OTHER PUBLICATIONS

"Particle Size Measurement", by Terence Allen, Senior Lecturer in Powder Technology Unversity of Bradford (4 pages).
"Methods of Generating Solid Aerosols", Silverman and Billings, Journal, Aug. 1956, pp. 76–83.
"A New Dust Generator for Inhalation Toxicological Studies", Leong and Powell, The Upjohn Company, Kalamazoo, MI, pp. 157–168.
Physicians' Desk Reference to Pharmaceutical Specialties and Biologicals, (6 pages, including 571, 768, 968, 969, 1222, and cover page).
"New Principle in Powder Filling", Modern Packaging, Jul., 1962 (2 pages).
The brochure described in the Accofil™ Powder Filling Machinery from Perry Industries (2 pages).
"Dispensing Dry Materials Accurately" by Aronson of Perry Industries (1966) pp. 2–9.
"Particulate Technology" by Clyde Orr, Jr. (1966) pp. 106, 107, 160, 161, 164, 165, 400, 401, 408 and 409.
International Search Report dated Mar., 31, 1993.

*Primary Examiner*—Aaron J. Lewis
*Attorney, Agent, or Firm*—Jeffrey J. Hohenshell

[57] ABSTRACT

A novel powdered medicament dispenser is disclosed. The powder medicament dispenser includes a novel agglomerator for loading the powder from a reservoir to a dispensing mechanism. In another aspect of the invention, a disposable cartridge is disclosed for use with a medicament dispenser having pressurization and actuator assemblies. A novel method of dispensing a powdered medicament, as well as inhalation activated and transmission assemblies are also disclosed.

44 Claims, 26 Drawing Sheets

U.S. PATENT DOCUMENTS

| | | | |
|---|---|---|---|
| 3,456,644 | 7/1969 | Thiel . | |
| 3,456,645 | 7/1969 | Brock . | |
| 3,456,646 | 7/1969 | Phillips et al. . | |
| 3,565,070 | 2/1971 | Hanson et al. | 128/173 |
| 3,598,294 | 8/1971 | Hedrick et al. | 222/402.2 |
| 3,605,738 | 9/1971 | Ciranna . | |
| 3,636,949 | 1/1972 | Kropp | 128/173 R |
| 3,704,816 | 12/1972 | Gandrud | 222/368 |
| 3,732,864 | 5/1973 | Thompson et al. | 128/173 R |
| 3,789,843 | 2/1974 | Armstrong et al. | 128/173 R |
| 3,809,084 | 5/1974 | Hansen | 128/266 |
| 3,814,297 | 6/1974 | Warren | 222/402.13 |
| 3,826,413 | 7/1974 | Warren | 222/402.13 |
| 3,921,637 | 11/1975 | Bennie et al. | 128/266 |
| 4,003,500 | 1/1977 | Schorning | 222/133 |
| 4,046,146 | 9/1977 | Rosskamp et al. | 128/266 |
| 4,177,941 | 12/1979 | Leong | 222/636 |
| 4,200,099 | 4/1980 | Guenzel et al. | 128/266 |
| 4,414,972 | 11/1983 | Young et al. | 128/200.23 |
| 4,446,862 | 5/1984 | Baum et al. | 128/203.15 |
| 4,524,769 | 6/1985 | Wetterlin | 128/203.15 |
| 4,534,345 | 8/1985 | Wetterlin | 128/203.15 |
| 4,570,630 | 2/1986 | Elliot et al. | 128/203.15 |
| 4,576,157 | 3/1986 | Raghuprasad | 128/200.23 |
| 4,592,348 | 6/1986 | Waters, IV et al. | 128/200.23 |
| 4,648,393 | 3/1987 | Landis et al. | 128/200.14 |
| 4,664,107 | 5/1987 | Wass | 128/200.23 |
| 4,667,668 | 5/1987 | Wetterlin | 128/203.15 |
| 4,803,978 | 2/1989 | Johnson, IV et al. | 128/200.23 |
| 4,817,822 | 4/1989 | Rand et al. | 222/38 |
| 4,860,740 | 8/1989 | Kirk et al. | 128/203.15 |
| 4,907,583 | 3/1990 | Wetterlin et al. | 128/203.15 |
| 5,027,808 | 7/1991 | Rich et al. | 128/203.23 |
| 5,033,463 | 7/1991 | Cocozza | 128/203.21 |
| 5,048,514 | 9/1991 | Ramella | 128/203.21 |
| 5,060,643 | 10/1991 | Rich et al. | 128/200.23 |
| 5,069,204 | 12/1991 | Smith et al. | 128/200.23 |
| 5,113,855 | 5/1992 | Newhouse | 128/203.12 |
| 5,119,806 | 6/1992 | Palson et al. | 128/200.14 |
| 5,161,524 | 11/1992 | Evans | 128/203.15 |
| 5,224,472 | 7/1993 | Pesenti et al. | 128/200.23 |
| 5,239,992 | 8/1993 | Bougamont et al. | 128/203.15 |
| 5,239,993 | 8/1993 | Evans | 128/203.15 |
| 5,243,970 | 9/1993 | Ambrosio et al. | 128/203.15 |
| 5,320,714 | 6/1994 | Brendel | 128/203.15 |

FOREIGN PATENT DOCUMENTS

| | | |
|---|---|---|
| 453 566 | | |
| 24 40 623 | 3/1976 | Germany . |
| 30 40 641 | 5/1982 | Germany . ...... 2/1988 ..... Sweden . |
| 1 269 544 | 4/1972 | United Kingdom . |
| 1 269 811 | 4/1972 | United Kingdom . |
| 1 335 378 | 10/1973 | United Kingdom . |
| 1 383 761 | 2/1975 | United Kingdom . |
| 2 084 960 | 4/1982 | United Kingdom . |
| 2 204 799 | 11/1988 | United Kingdom . |
| 2 233 236 | 1/1991 | United Kingdom . |
| 2 251 898 | 7/1992 | United Kingdom . |
| 2 253 200 | 9/1992 | United Kingdom . |
| 2 233236 | 5/1993 | United Kingdom . |
| 82/01133 | 4/1982 | WIPO . |
| WO 90/07351 | 7/1990 | WIPO . |
| 0 407 276 | 1/1991 | WIPO . |
| WO 91/02558 | 3/1991 | WIPO . |
| WO 91/06333 | 5/1991 | WIPO . |
| WO 91/12040 | 8/1991 | WIPO . |
| WO 91/12895 | 9/1991 | WIPO . |
| WO 92/00771 | 1/1992 | WIPO . |
| WO 92/03175 | 3/1992 | WIPO . |
| WO 92/04067 | 3/1992 | WIPO . |
| WO 92/04068 | 3/1992 | WIPO . |
| 92/04928 | 4/1992 | WIPO . |
| WO 92/05823 | 4/1992 | WIPO . |
| WO 92/05824 | 4/1992 | WIPO . |
| WO 92/06727 | 4/1992 | WIPO . |
| WO 92/09322 | 6/1992 | WIPO . |
| WO 92/10228 | 6/1992 | WIPO . |
| WO 92/10229 | 6/1992 | WIPO . |
| WO 92/12799 | 8/1992 | WIPO . |
| WO 91/13646 | 9/1992 | WIPO . |
| WO 92/15353 | 9/1992 | WIPO . |
| WO 92/17231 | 10/1992 | WIPO . |
| WO 92/17232 | 10/1992 | WIPO . |
| WO 92/18188 | 10/1992 | WIPO . |

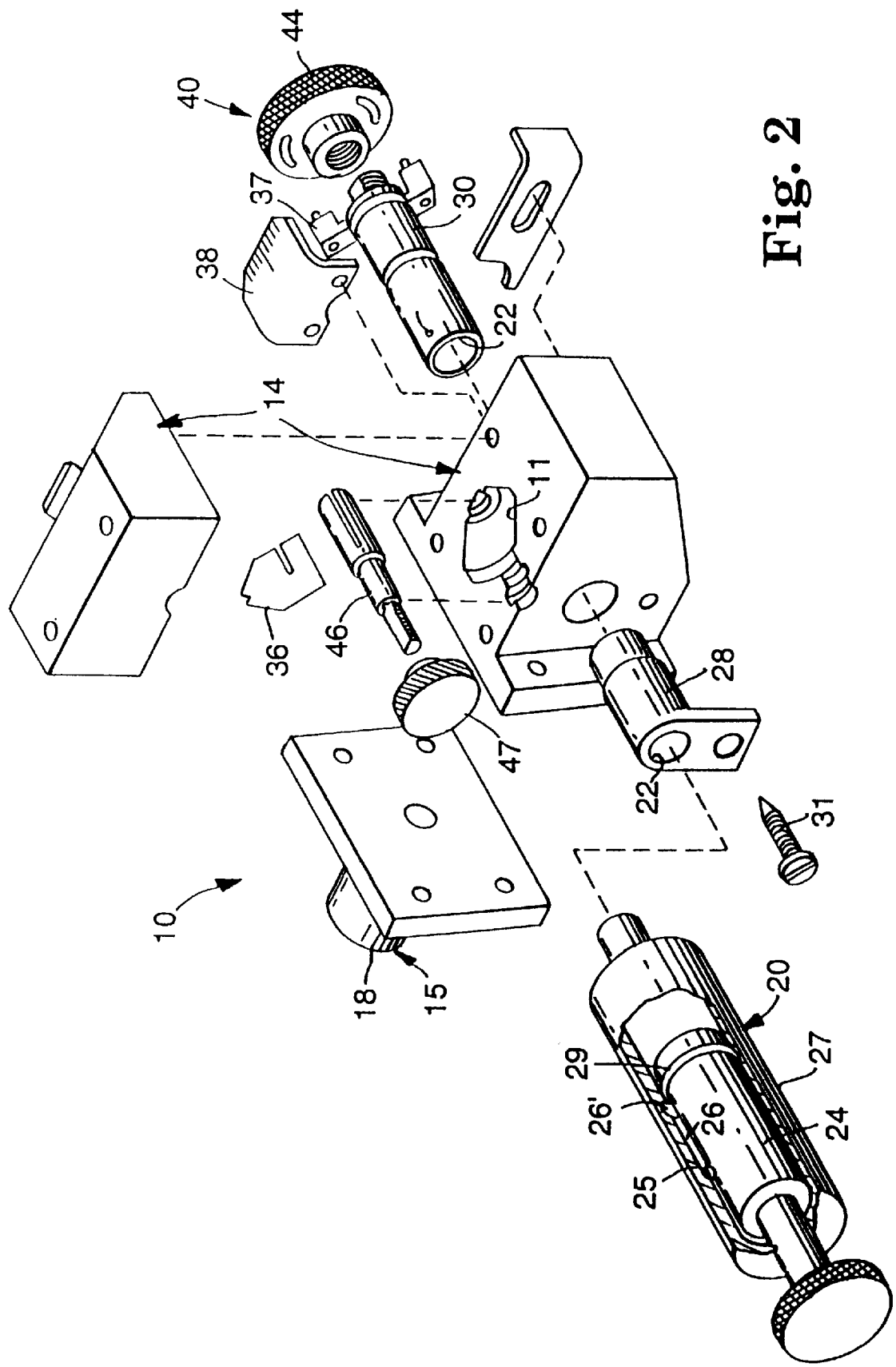

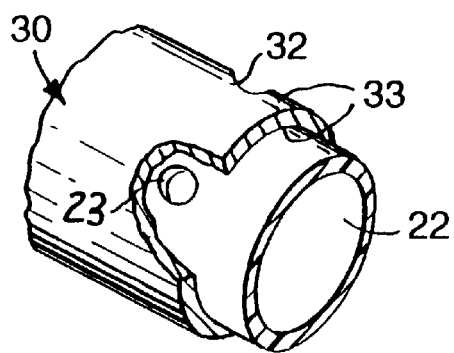
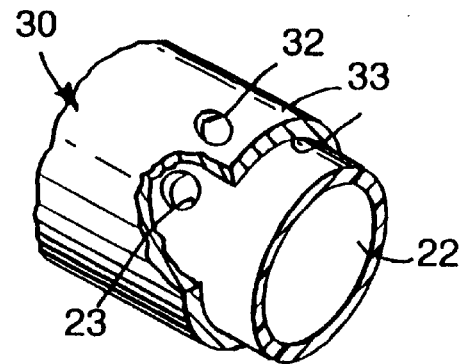
Fig. 6
Fig. 7
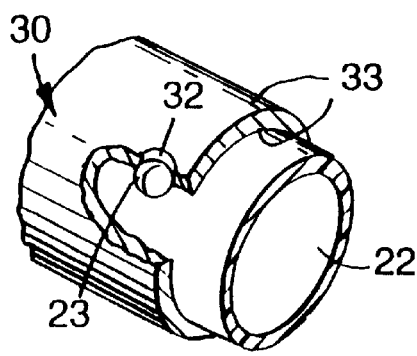
Fig. 8
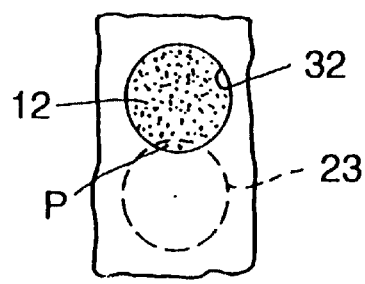
Fig. 9

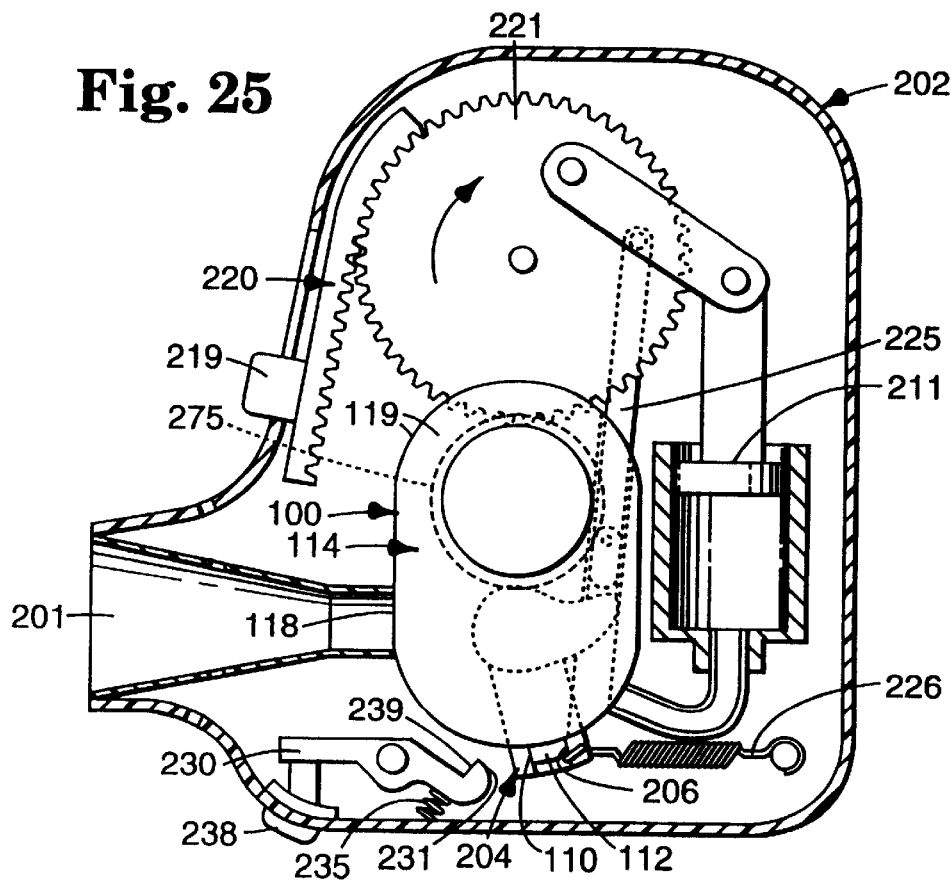
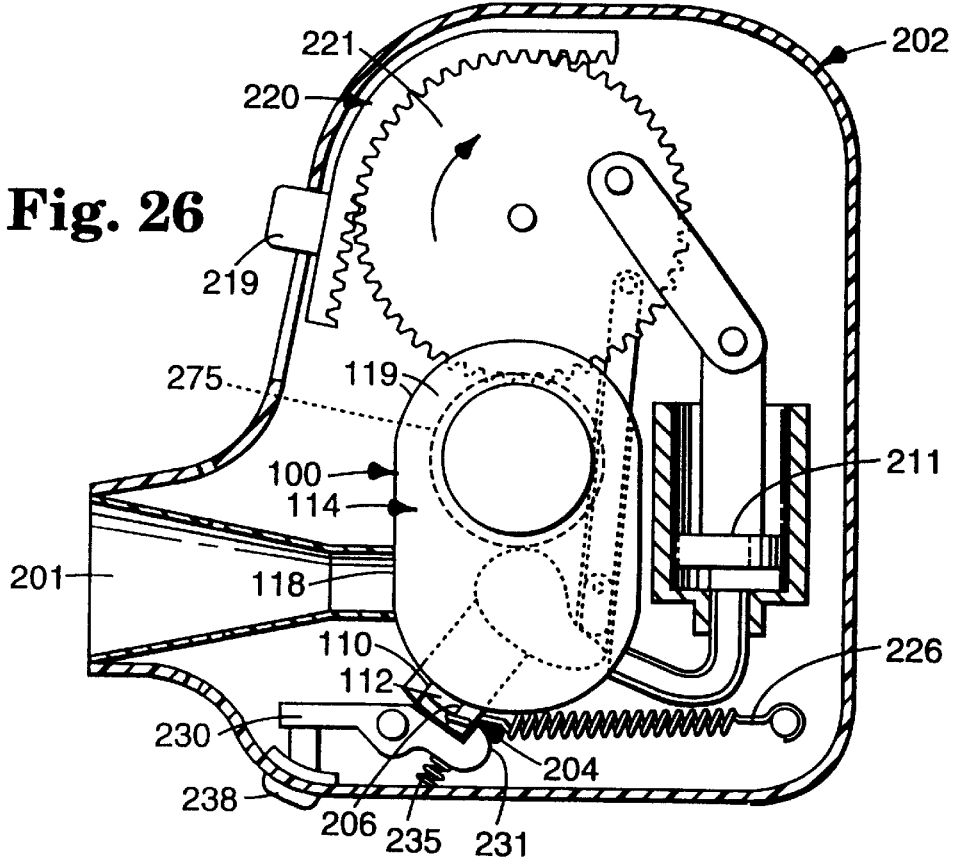

POWDER DISPENSER

This application is a continuation of U.S. patent application Ser. No. 07/975,625, filed Nov. 12, 1992, (the '625 application) which '625 application (now abandoned) was a continuation-in-part of U.S. patent application Ser. No. 07/817,331 filed Jan. 6, 1992 (now abandoned) and U.S. patent application Ser. No. 07/749,912 filed Aug. 26, 1991 (now abandoned) and U.S. patent application Ser. No. 07/817,331 is a continuation-in-part application of U.S. patent application Ser. No. 07/749,912.

TECHNICAL FIELD

The present invention relates generally to devices which facilitate the inhalation of dry powder medicament.

BACKGROUND OF THE INVENTION

The popularity of the use of medicaments in dry powder form is increasing at least to some extent due to the search for a replacement for dispensing devices which utilize chlorofluorocarbons to deliver a pharmaceutically active compound. Chlorofluorocarbons are said to have an adverse effect on the earth's ozone layer, but the use of a chlorofluorocarbon as a propellant in a medicament dispensing device is also undesirable for other reasons. For example, some drug compounds are incompatible with chlorofluorocarbons.

The popularity of micronized dry powder medicaments is increasing even in light of their tendency to resist flow due to factors such as static conditions, humidity conditions and the effect of van der Waal's forces between the particles. Additionally, micronized, dry powder medicaments generally tend to pack into unduly large agglomerates. If the medicament is delivered to a user in unduly large agglomerates, the large agglomerates tend to impinge on the tissue at the back of the user's throat thereby preventing the medicament from reaching the user's lungs. Such impact also tends to cause an uncomfortable "gag" reflex or coughing.

The dose of a dry powder medicament that is ultimately delivered to a user should be dispersed to maximize the respirable fraction and efficacy of the medicament delivered to the user and to avoid the attendant problems associated with large agglomerates of powder. Rosskamp et al. U.S. Pat. Nos. 4,046,146; 4,811,731 to Newell et al.; U.S. Pat. No. 2,587,215 to Priestly and U.S. Pat. No. 4,524,769 to Wetterlin all describe inhalators that are powered by the user's inhalation airflow. One problem associated with user powered dispensers is that the user's capacity to generate an effective airflow may be adversely affected by an ailment such as bronchial asthma. It is believed that the powder medicament dispensers which rely upon user generated airflow tend to be inefficient, particularly when a user's capacity to generate an inhalation airflow is adversely affected by an ailment. Another problem associated with user powered dispensers is that different persons possess widely varying abilities to generate inhalation airflows. Requiring some users to generate a considerable airflow may cause discomfort.

Wetterlin U.S. Pat. No. 4,524,769 describes a device similar to a TURBOHALER™ dispenser which is generally available from Aktiebolaget Draco, of Lund, Sweden and has been on sale in Europe. That device includes a perforated member with a plurality of perforations for each dosage of medicament. The TURBOHALER™ dispenser is a user powered inhalation device and is believed to suffer from the problems associated with user powered medicament dispensers mentioned above.

DISCLOSURE OF THE INVENTION

The present invention provides a simplified dry powder medicament dispenser which: (1) includes a novel assembly which provides the dry powder medicament in a dosage chamber in a packed, agglomerated form to thereby contribute to dose uniformity by repeatably providing a precisely metered dose of the medicament, (2) effectively and efficiently dispenses and disperses dry powder medicament into the inhalation airstream of a user even when that inhalation airflow is at a rate that is less than the rate of an average person, (3) affords a highly efficient airflow within the dispenser to dispense and disperse the dry powder medicament, (4) wastes very little medicament, and (5) provides repeatable dosage accuracy.

According to one aspect of the present invention, there is provided a dry powder medicament dispenser for reproducibly dispensing multiple, individual doses of micronized particles of a dry powder medicament to the respiratory system of a user. The dispenser comprises a housing, means for providing an agglomerated, predetermined dose of powdered medicament within a dosage chamber of a dosage member, a pressurization assembly, and an actuator.

The dosage chamber defines a powder loading axis. The means for providing an agglomerated, predetermined dose preferably comprises a medicament reservoir for holding a bulk supply of dry powder medicament, and an agglomerator for engaging powder within the medicament reservoir. More preferably, the agglomerator is mounted to move across the dosage chamber to provide a positive powder packing force that has a component which is generally parallel to the loading axis to transfer dry powder medicament from the medicament reservoir to the dosage chamber and to pack the dry powder medicament into the agglomerated, predetermined dose in the dosage chamber. The packing force increases as the agglomerator moves across at least a portion of the dosage chamber. Preferably, the agglomerator comprises a flexible blade which progressively, increasingly bends to increase the component of the packing force which is parallel to the loading axis as the blade moves across at least a portion of the dosage chamber. The blade packs the powder into a reproducible dose which contributes to dose uniformity by repeatably providing a precisely metered dose of the medicament.

Once the dose is provided in a packed, agglomerated form, the pressurization assembly is utilized to deagglomerate the dose. The pressurization assembly includes a pressurization member for reproducibly generating a deagglomeration pressure sufficient to deagglomerate the dose within the dosage chamber, a pressure reservoir for intermittently storing the deagglomeration pressure, and a pressure outlet for releasing the deagglomeration pressure from the pressure reservoir. Preferably, the dosage member comprises a sealing surface for sealing the pressure outlet so that the pressure reservoir may store the deagglomeration pressure.

The actuator registers the pressure outlet and the dosage chamber in a registered position so that the deagglomeration pressure forcibly expels the predetermined, agglomerated dose from the dosage chamber in deagglomerated form suitable for inhalation therapy. Preferably, the actuator registers the pressure outlet with the dosage chamber by moving progressively increasing portions of the pressure outlet and the dosage chamber into alignment to expose progressively increasing portions of the dosage chamber to the deagglomeration pressure. Also, in the registered position, the dosage chamber is situated generally immediately adjacent the pressure outlet.

Preferably, the device further includes a medicament delivery passageway which affords passage of the dose that has been expelled from the dosage chamber. The medicament delivery passageway is substantially free of structure for deagglomerating the powder beyond the deagglomeration provided by the pressurization assembly.

According to a second aspect of the present invention there is provided a cartridge which (1) is adapted to be received in and cooperate with remaining portions of a dry powder medicament dispenser; (2) may be replaced in the dry powder medicament dispenser with another cartridge after it is depleted; (3) affords re-use of the dispenser with a number of different cartridges; (4) may be constructed to restrict tampering with the dry powder medicament; and (5) optionally includes a counter assembly which affords an estimate of the number of dosages of medicament available in the cartridge.

The housing includes an inhalation airway passageway affording passage of a user inspiratory airflow. According to a third aspect of the present invention, the actuator comprises a biasing means such as a spring for biasing the dosage chamber toward the registered position, and releasable retaining means for releasably retaining the dosage chamber spaced from the registered position against the bias of the spring. The releasable retaining means preferably comprises an inhalation activated system in communication with the inhalation airway passageway. The inhalation activated system releases the dosage chamber in response to the user inspiratory airflow to afford movement of the dosage chamber to the registered position under the bias of the spring.

The dosage chamber is preferably movable relative to the pressure outlet between (1) a load position with the dosage chamber in communication with the medicament reservoir and (2) the registered position. Also, the pressurization member is preferably movable between retracted and extended positions such that (1) movement of the pressurization member from the extended toward the retracted position draws ambient air into the pressure reservoir, and (2) movement of the pressurization member from the retracted toward the extended position pressurizes air within the pressure reservoir.

According to a fourth aspect of the present invention, the device includes a handle movable relative to the housing, and a transmission for transmitting the movement of the handle to the pressurization member, dosage chamber and agglomerator. Preferably, the handle is movable relative to the housing between first and second positions. In a preferred embodiment, movement of the handle from the first toward the second position: (1) moves the pressurization member from the extended to the retracted position, and (2) moves the dosage member from the registered to the load position against the bias of the spring and so that the sealing surface seals the pressure outlet. Movement of the handle from the second toward the first position (1) moves the pressurization member from the retracted to the extended position to pressurize the pressure reservoir to the deagglomeration pressure, and (2) causes the agglomerator to transfer the powder from the medicament reservoir to the dosage chamber.

The present invention may also be described as a method of dispensing multiple individual doses of a dry powder medicament comprising the steps of (1) packing micronized particles of the medicament within a dosage chamber into a predetermined, agglomerated dose, (2) generating a deagglomeration fluid pressure sufficient to deagglomerate the dose within the dosage chamber, (3) intermittently storing the deagglomeration fluid pressure in a pressure reservoir having a pressure outlet for releasing the deagglomeration fluid pressure, and (4) forcibly expelling the dose from the dosage chamber with the deagglomeration pressure in a deagglomerated form suitable for inhalation therapy by registering the pressure outlet and the dosage chamber.

BRIEF DESCRIPTION OF THE DRAWING

The present invention will be further described with reference to the accompanying drawing herein like reference numerals refer to like parts in the several views, and wherein:

FIG. 2 is an exploded perspective view of the dispenser of FIG. 1 rotated approximately ninety-degrees and showing a piston for pressurizing a fluid pressure reservoir;

FIGS. 6 through 8 are enlarged fragmentary perspective views of parts of the dispenser of FIG. 1 which sequentially illustrate movement of a dosage chamber into alignment with a pressure outlet passageway;

FIG. 9 is an enlarged fragmentary schematic illustration of initial alignment of a dosage chamber with the outlet passageway that occurs during the sequence illustrated in FIGS. 6–8;

FIGS. 25 and 26 are schematic representations of an example of a medicament dispenser for use with the cartridge of the present invention which sequentially illustrate the operation of the cartridge in conjunction with the dispenser;

FIGS. 33 through 35 are perspective, partial sectional views of different sections of the dispenser according to the fourth aspect of the present invention, which sequentially illustrate the operation of a transmission according to the present invention wherein:

FIG. 33 illustrates a dosage chamber and a pressure outlet in a registered position, and a handle in a first position;

FIG. 34 illustrates the handle in a second position, and the dosage chamber spaced from the registered position and in a position to receive medicament; and FIG. 35 illustrates the handle after it has been returned to the first position;

DETAILED DESCRIPTION OF THE PREFERRED EMBODIMENTS

Figure 1:
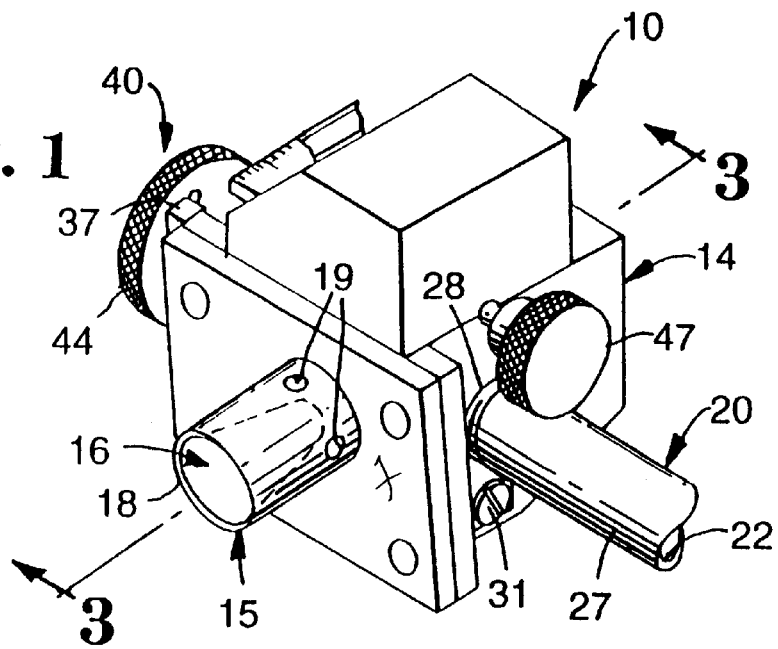
FIG. 1 is a perspective fragmentary view of one embodiment of dispenser according to the present invention shown from its front side.

Referring now to FIGS. 1 through 12 of the drawing, there is shown one embodiment of dispenser according to the present invention, generally designated by the reference number 10. The dry powder medicament dispenser 10 reproducibly dispenses multiple, individual doses of micronized particles of a dry powder medicament for ultimate delivery to the respiratory system of a user.

The dispenser comprises a housing 14 having inner and outer 8 surfaces, means for providing an agglomerated, predetermined dose of powdered medicament within a dosage chamber 32 of a dosage member 30, a pressurization assembly 20 for providing a deagglomeration pressure, an actuator 40, and an optional mouthpiece portion 15.

The pressurization assembly 20 preferably includes a pressure reservoir 22, a pressure outlet 23 and a pressurization member 24. The actuator 40 registers the pressure outlet 23 and the dosage chamber 32 in a registered position (FIG. 5) so that the deagglomeration pressure forcibly expels the predetermined, agglomerated dose from the dosage chamber 32 in deagglomerated form suitable for inhalation therapy (note the arrows in FIG. 5). The deagglomeration pressure is utilized to deagglomerate the powder into primary (substantially micronized) particles, thereby providing an effectiveness in deagglomerating the packed dose which is generally independent of patient inhalation rate. Thus, a respirable mass of the dry powder medicament may consistently be provided to a patient, even at reduced patient inhalation airflow rates.

The dosage chamber 32 defines a powder loading axis f (FIG. 3) which is preferably normal to the surfaces of the dosage member 30 that define an end of the dosage chamber 32. The means for providing an agglomerated, predetermined dose is described in greater detail below and preferably comprises a medicament reservoir 11, and an agglomerator (e.g. 36, 46) for engaging powder 12 within the medicament reservoir 11.

The dispenser 10 facilitates oral inhalation of powdered medicaments 12 that are stored in bulk form in medicament reservoir 11. The powdered medicaments 12 may be from any suitable therapeutic category such as, but not limited to antibiotics, proteins/peptides, steroids, bronchodilators, anticholinergics, lipoxygenase inhibitors, PAF antagonists, potassium channel activators, mast cell stabilizers, bradykinin analogs, enkephalins or interleukin. As examples not intended to be limiting, the powder may be leuprolide, albuterol, insulin, pirbuterol, beclomethasone, terbutaline, salmeterol, fluticasone, tiamcinolone, salbutamol, isoproterenol, epinephrine, fenoterol, formoterol, procaterol, pentamidine, calcitonin, ipratropium, oxitropium, budesonide or their pharmaceutically acceptable salts.

The dry powder medicament dispenser 10 is particularly suited for delivery of a predetermined dosage unit comprising a plurality of very fine particles having an average diameter as low as about 0.3 micrometers or even possibly less. Generally, by "very fine" or "micronized" particles, an average particle diameter is contemplated with a range of from about 0.3 micrometers to about 20 micrometers, and preferably from about 0.5 micrometers to about 6.0 micrometers. Alternatively, such particles can be described as microfine particles. For example, a dose of the powdered medicament 12 may comprise 0.115 milligrams of a solid micronized albuterol sulfate powder having an average particle size of approximately 3 micrometers.

The dispenser 10 includes (1) an optional medicament delivery passageway 16 extending between an injection inlet end 17 (e.g. a circular opening having a diameter of 0.062 inches (1.57 millimeters) formed by a bore in the housing 14) intermittently communicating with the dosage chamber 32, and an outlet end 18 opening through the mouthpiece portion 15, (2) at least one air entrance passageway 19 having an inlet end opening through the outer surface 8 of the housing 14 and an outlet end opening into the medicament delivery passageway 16, and (3) the pressure outlet passageway 23 with an inlet end communicating with the fluid pressure reservoir 22 and an outlet end opening generally opposite the injection inlet end 17 of the medicament delivery passageway 16.

The housing 14 may be constructed from any suitable metal or polymeric material approved by the U.S. Food and Drug Administration for medical purposes, such as but not limited to polyacetal, polyethylene, Plexiglas™, polypropylene, polycarbonate, or combinations thereof. As particular examples, not intended to be limiting, the housing 14 may be constructed from the polycarbonate grade # HP-1 LEXAN™, generally available from General Electric of Pittsfield Mass. or Plexiglas™ generally available from Rhom & Haas.

The "movable chamber means" or dosage member 30 may be a cylindrical tubular member having an inner diameter of 8.46 millimeters (0.333 inches) and a wall thickness of 0.46 millimeters (0.018 inches). Alternatively, the dosage member 30 may comprise a generally flat, planar structure having a thickness of about 0.46 millimeters (0.018 inches).

In a preferred embodiment, the dosage member 30 has an outer sealing surface 33 and includes surfaces defining the dosage chamber 32 having the longitudinal axis f. The dosage chamber 32 extends through the dosage member 30 between spaced parts of the outer sealing surface 33 (see FIGS. 3–5).

The volume of the dosage chamber 32 is influenced by a variety of factors but is particularly influenced by the type of powdered medicament that is intended to be delivered. For example, when 0.115 mg. of albuterol sulfate is to be dispensed from the dosage chamber 32, the volume of the dosage chamber 32 should be approximately 0.24 cubic millimeters. Also as an example, if the dosage chamber 32 is cylindrical, the dosage chamber may have a diameter of about 0.032 inches for a dosage member 30 that is 0.018 inches thick.

The cross-section of the dosage chamber 32 illustrated is circular to form a cylindrical passageway. Alternatively the dosage chamber 32 may have any suitable cross sectional shape such as, but not limited to triangular, square, star, hexagonal, arcuate, polygonal, or shapes formed by combinations of straight and arcuate line segments. The cross-section may remain uniform throughout the dosage member 30 or may taper. Preferably, there is a single dosage chamber 32 that provides a consistent dosage receiving volume which tends to receive consistent volumes of powdered medicament to thereby contribute to repeatable dosage accuracy.

The cross-section of the dosage chamber 32 is preferably slightly smaller than the cross-section of the pressure outlet passageway 23 to afford complete expulsion of the medicament 12 from the dosage chamber 32, and to insure proper communication between the pressure outlet passageway 23 and the dosage chamber 32. For example, if the cross-section of the dosage chamber 32 is circular having a diameter of approximately 0.032 inches (0.81 millimeters), then the cross-section of the pressure outlet passageway 23 may also be circular with a diameter of approximately 0.052 inches (1.32 millimeters) or even 0.055 inches (1.40 millimeters). Generally, the cross-section of the injection inlet 17 for the medicament delivery passageway 16 preferably has approximately the same or larger cross-sectional area than the cross-sectional area of the dosage chamber 32. For a circular cross-section of the dosage chamber 32 with a diameter of approximately 0.032 inches (0.81 millimeters), the cross-sectional area of the injection inlet 17 may also be circular with a diameter of approximately 0.062 inches (1.57 millimeters).

The dosage member 30 may be constructed from any suitable material approved by the U.S. Food and Drug Administration for medical purposes such as, but not limited to, polymeric, plastic or metal materials or combinations thereof. For example, the dosage member may be constructed from Grade #M90 CELCON™ generally available from HOECHST CELANESE or an appropriate stainless steel. The material used to construct the dosage member 30 and housing 14 should be sufficiently strong to resist deformation upon pressurization of the pressure reservoir 22.

As best seen in FIGS. 6 through 9, the dosage member 30 is preferably mounted adjacent inner portions of the housing 14. Those portions (see FIG. 6) may comprise a part 28 which also forms portions of the fluid pressure reservoir 22. Preferably the end of the part 28 adjacent gas pressure release outlet or aperture 23 has a closed end to form the pressure reservoir 22.

Means such as elastomeric sealing gaskets (not shown) may provide a seal between the dosage member 30 and the medicament reservoir 11 to prevent leakage or escape of powder 12 from the reservoir 11. Alternatively the means for preventing escape of powder 12 could comprise biasing means such as a screw for biasing the dosage member 30 into tight frictional engagement with the inner surfaces of housing 14.

The means for providing an agglomerated, predetermined dose preferably utilizes a novel powder loading assembly that contributes to consistent dosage accuracy. That means comprises an agglomerator for transferring a predetermined quantity of the dry powder medicament 12 from the medicament reservoir 11 to the dosage chamber 32 and for packing the predetermined quantity into an agglomerated dose within the dosage chamber 32.

The agglomerator preferably includes a flexible, resilient powder loading blade 36 situated at least partially within the medicament reservoir 11 for providing a positive packing force that has a component which is generally parallel to the loading axis f. As described below, the packing force preferably increases as the blade 36 moves across at least a portion of the chamber 32, and more particularly, the flexible blade 36 preferably progressively, increasingly bends to increase the component of the packing force which is generally parallel to the loading axis f as the blade 36 moves across at least a portion of the chamber 32.

When the dispenser 10 is used to dispense micronized particles of a dry powder drug 12, the micronized particles tend to resist flow from the medicament reservoir 11 into the dosage chamber 32 due to naturally occurring (ambient) forces. It is believed that factors such as the effect of static and humidity conditions, and the effect of cohesion (e.g. van der Waals forces) contribute to the medicament's resistance to flow. For at least some powdered medicaments, the packing force can be described as an orientation independent packing force because it is greater than and overcomes ambient forces. Those ambient forces include van der Waals forces between the micronized particles, gravity and the deleterious effects of static and humidity conditions on the flow characteristic of the micronized particles. Thus, for at least some powdered medicaments, the packing force will reproducibly load the medicament 12 into the dosage chamber 32 even in a sideways or inverted orientation.

Packing the dosage chamber 32 is believed to contribute to repeated, consistent dosage accuracy as the chamber 32 is consistently loaded with generally the same amount of medicament. At least one and preferably four flexible loading blades 36 are provided, each having proximal and distal 39 ends and a leading or "major" surface between the proximal and distal ends. The blades 36 are mounted on a shaft or hub 46 having generally the same axis as the axis of the medicament reservoir 11.

The blades 36 are constructed from any suitable flexible material including but not limited to polymers, metals or polyesters. As a particular example, not intended to be limiting, the blades may be constructed from a polyetherimide material such as grade #1000 ULTEM™ generally available from General Electric of Pittsfield, Mass. The powder loading blades 36 may have a length from the axis of the medicament reservoir 11 of approximately 0.315 inches.

While the blades 36 should be flexible to bend as described in more detail below, the blades should nevertheless be sufficiently stiff to exert a force on the dosage member 30 when the blade moves across the dosage member 30. Preferably, a blade has a sufficient stiffness to provide a force between about 0.01 pounds and about 2 pounds on the dosage member (e.g. 30) when the blade moves across the dosage member. More preferably, a blade should have a sufficient stiffness (modulus of elasticity) to provide between about 0.4 and 0.8 pounds of force.

The blade turning shaft 46 is rotated by a powder loading knob 47. Rotation of the knob 47 while the dosage chamber 32 opens into the medicament reservoir 11 causes revolving movement of the blades 36 that scrapes medicament 12 from the walls of the reservoir 11, simultaneously loads the dosage chamber 32 with a dosage of dry powder medicament 12 and also tends to agitate the powder 12 to break the powder 12 into smaller agglomerates.

Figure 3:
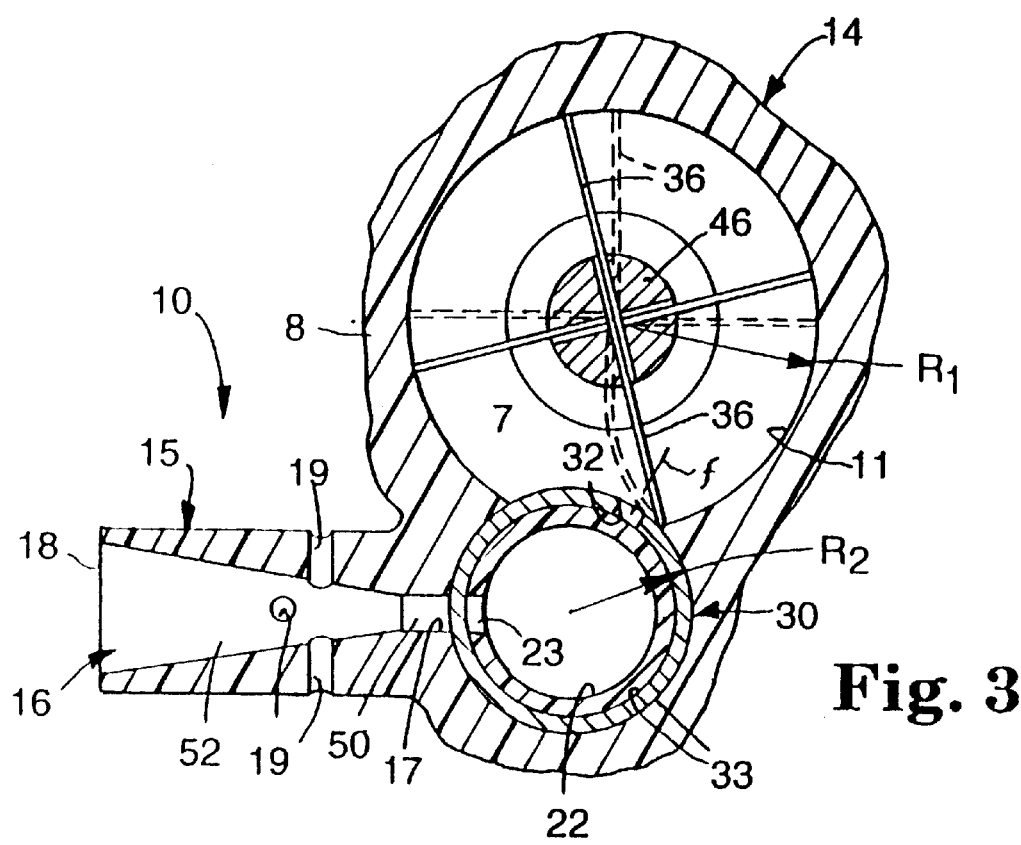
FIGS. 3 through 5 are enlarged sectional views of the device of the present invention taken approximately along lines 3—3 of FIG. 1 with portions broken away to show details and which sequentially illustrate the delivery of medicament to a user.
Figure 4:
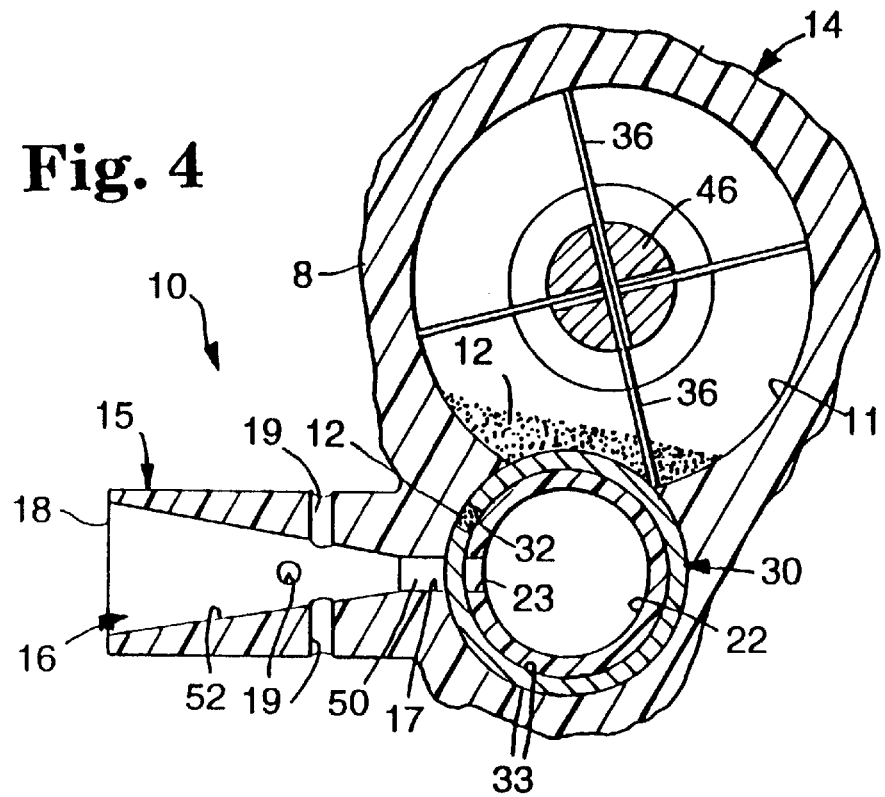
Figure 5:
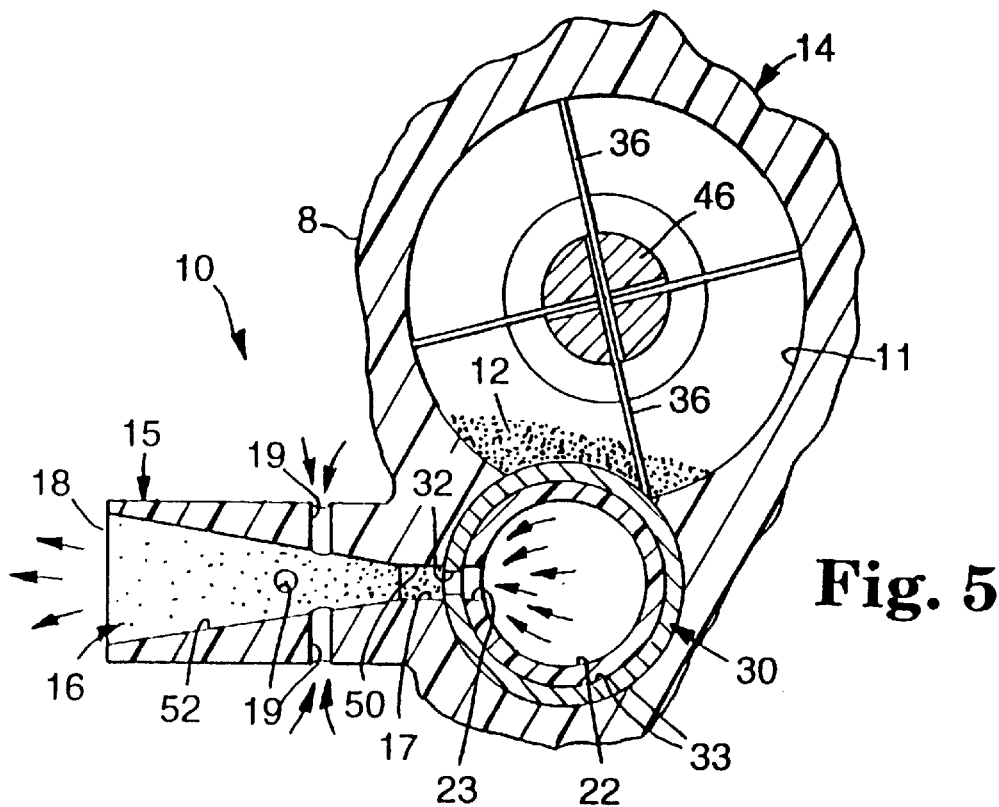
Figure 10:
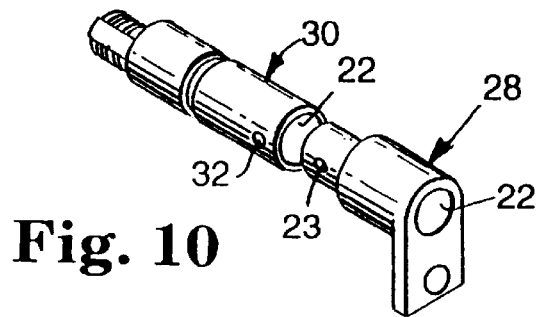
FIG. 10 is a perspective view of portions of a dosing member and a pressurization member which are preferably included in the dispenser of FIG. 1.
Figure 11:
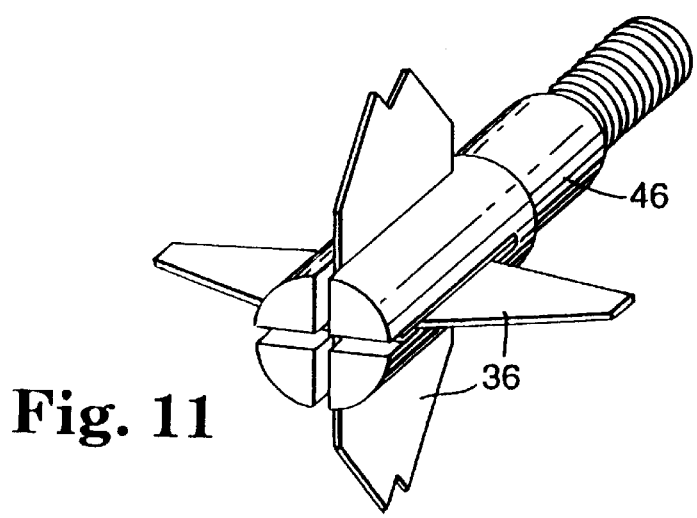
FIG. 11 is a perspective view of loading blades on a support shaft which are preferably included in the dispenser of FIG. 1.

The shaft or core 46 moves the flexible blades 36 along a predetermined path within the medicament reservoir 11 with the leading surface leading and the distal end 39 of the blade 36 moving along or adjacent to a portion of the inner surface defining the medicament reservoir 11 during a first portion of the predetermined path (FIG. 3, solid line). During a second portion (FIG. 3 dashed lines) of the predetermined path, the distal end 39 of the blade 36 moves along a portion of the outer sealing surface 33 of the dosage member 30 which results in progressively increasing bending of the blade 36 to form the leading surface into a convex surface and to move the leading surface progressively closer to the outer sealing surface 33 of the dosage member 30. When the distal end 39 of the blade 36 is described as moving along a portion of the outer sealing surface 33 of the dosage member 30, it is herein contemplated that a thin layer of powder 12 (e.g. 0.01 inches) may be present between the distal end of the blade 36 and the dosage member 30.

The medicament reservoir 11 is generally cylindrically concave and has a medicament reservoir axis which defines a reservoir radius R1 (FIG. 3).

The outer surfaces of the dosage member 30 along with its axis define a radius R2 (FIG. 3). As an example which is not intended to be limiting, the dosage member 30 may have a radius R2 of approximately 0.187 inches, the medicament reservoir 11 may have a radius R1 of approximately 0.32 inches, and the distance between the axes of the medicament reservoir 11 and the dosage member 30 may be about 0.47 inches.

The core 46 mounts the proximal ends of the blades 36 for revolving movement around the medicament reservoir axis. The portion of the outer sealing surface 33 of the dosage member 30 along which the distal end of the blade 36 moves is cylindrically concave about an axis generally parallel to the medicament reservoir axis R1.

The distance between the axes of the blade 36/medicament reservoir 11 and the dosage member 30 is less than the sum of the radii of the dosage member 30 and the medicament reservoir 11 (R1+R2) to afford interference between the powder loading blade 36 and the dosage member 30 during the second portion of the predetermined path so that the powdered medicament 12 is loaded into dosage chamber 32 in a direction that is generally in the direction of the longitudinal or loading axis f of the dosage chamber 32.

Figure 12:
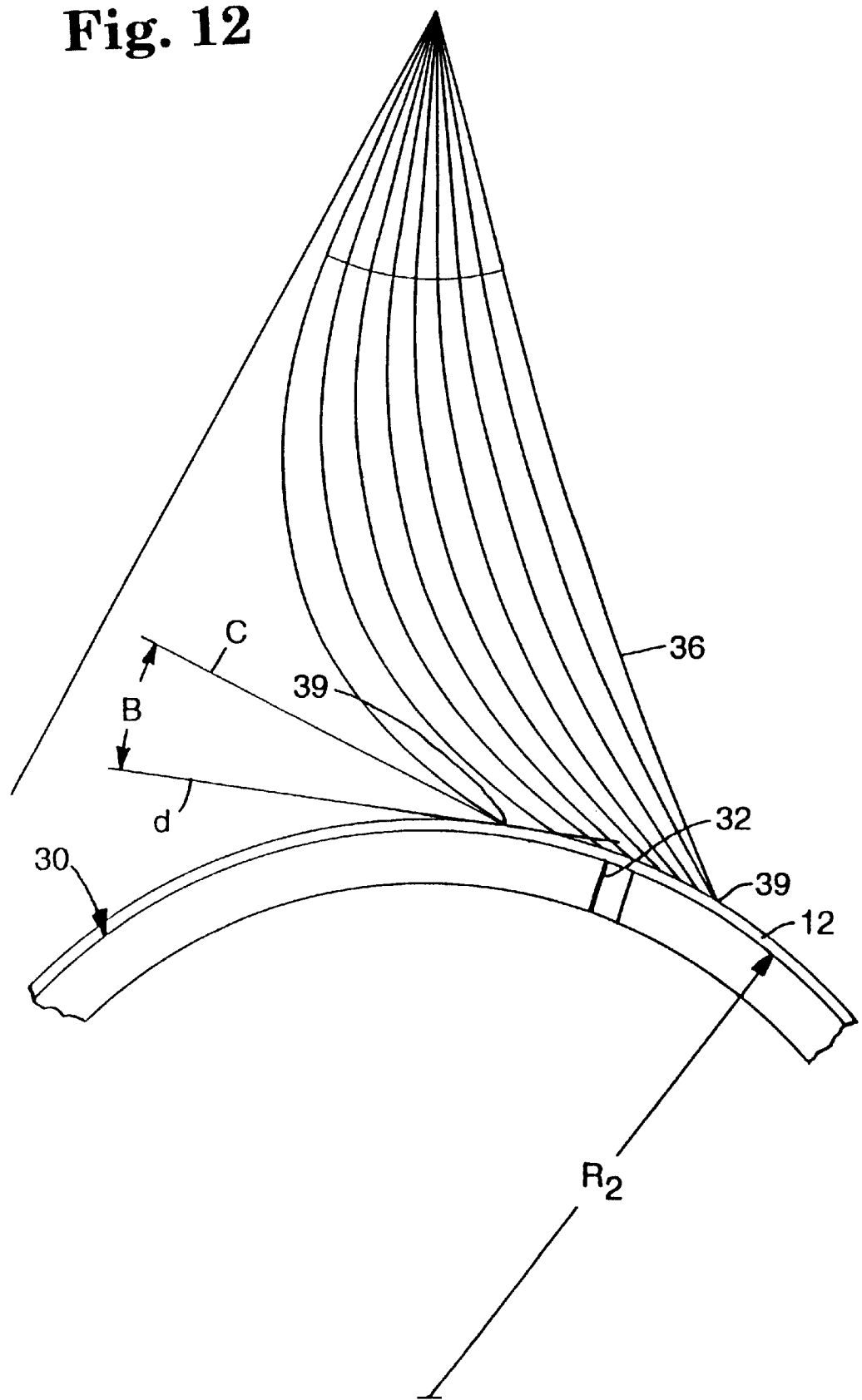
FIG. 12 is a computer simulation illustrating sequential movement of a loading blade relative to a dosage member.

FIG. 12 depicts a computer simulation of the powder loading assembly according to the present invention. To generate the computer simulation, a powder layer 12 of 0.01 inches was assumed to be present between the blade 36 and the dosage member 30. The simulation illustrates the position of the blade 36 for equal increments of rotation of core 46. When the flexible blade 36 engages the dosage member 30, the blade 36 will bend. At the line of contact between the blade 36 and the sealing surface of the dosage member 30 (or a thin layer of powder 12 directly adjacent thereto), there is an imaginary blade tangent line C that is tangent to the leading surface of the blade 36 and an imaginary dosage member tangent line d tangent to the outer sealing surface of the dosage member 30. The blade tangent line C and the dosage member tangent line d form a blade tangent angle Beta therebetween which progressively decreases as the blade 36 moves along at least a portion of the sealing surface and across at least a portion of the dosage chamber 32.

Just after the blade 36 encounters the dosage member 30, the action is similar to a rolling motion. As the blade moves across the dosage chamber 32, the blade tangent angle Beta progressively decreases so that the powdered medicament 12 is loaded into dosage chamber 32 in a direction that is generally along the loading axis f of the dosage chamber 32 (e.g. shown in FIG. 3 by the dashed lines). Forcing the powdered medicament in a direction generally along the axis f of the dosage chamber 32 is believed to repeatedly load the chamber with substantially uniform amounts of medicament 12 to thereby contribute to dosage accuracy.

Preferably, at least one of the loading blades 36 has a raking surface comprising a V-shaped notch (FIG. 11) in its distal end 39 that disperses agglomerates of the dry powder medicament 12 into smaller particles and separates the dry powder 12 from the walls of the medicament reservoir 11.

The pressurization assembly 20 is utilized to deagglomerate the dose that is packed into the dosage chamber 32. The pressurization assembly 20 includes the pressurization member (e.g. a piston 24) for reproducibly generating a deagglomeration pressure sufficient to deagglomerate the dose within the dosage chamber 32, the pressure reservoir 22 for intermittently storing the deagglomeration pressure, and the pressure outlet 23 for releasing the deagglomeration pressure from the pressure reservoir.

As used herein, when it is said that the pressurization assembly 20 "generates" a deagglomeration pressure, it is meant that the pressurization assembly creates the pressure used to expel the predetermined dose from the dosage chamber in situ, as opposed, for example, to a prepressurized container such as a cartridge or canister. The pressure reservoir 22 is preferably pressurized just before the powdered medicament is delivered to a user. Keeping the pressure reservoir 22 free of pressure between dose deliveries restricts wear on the elements of the dispenser 10.

The pressure outlet passageway 23 may be formed by a cylindrical bore in part 28. The part 28 may include a flange with an aperture to receive a screw 31 or any other suitable fastener to fix the part 28 in a proper position relative to the injection inlet opening 17 by firmly attaching the part 28 to the housing 14 so that the part 28 forms a portion of the inner surface of the housing 14. Alternatively the part 28 and the dispenser housing 14 may comprise a monolithic member such as an integrally molded member.

An example of the pressurization member is illustrated in FIG. 2 as a piston or plunger 24 having an O-ring 29 and a detent 25 adapted to be received in a channel or groove 26 in a fluid pressure member housing 27. An open end of the part 28 is adapted to receive a Luer fitting (not shown) or any suitable adapter for forming an air-tight attachment. The piston 24 pressurizes ambient air to the deagglomeration pressure. Use of ambient air as the fluid which is pressurized to provide the deagglomeration pressure affords a dispenser that is free of storage for a different deagglomeration fluid. While the pressurization assembly is shown in FIG. 2 to include a piston 24, it should be noted that the pressurization assembly 20 may comprise any suitable means for pressurizing fluid within the fluid pressure reservoir/chamber 22 above ambient pressure and for retaining the fluid pressure within the fluid pressure chamber 22 above ambient pressure including, but not limited to bellows, flexible bladders, or syringe/O-ring arrangements.

The groove 26 in the housing 27 has a first portion extending generally parallel to the axis of the fluid pressurization member housing 27 and a second locking portion 26' extending generally perpendicular to the first portion. To pressurize the fluid pressure reservoir 22, a user first sealingly covers the pressure outlet passageway 23 with surfaces 33 of the dosage member 30 (FIGS. 3 and 4) and then moves the piston 24 axially within the gas pressurization member housing 27 toward the housing 14 until the detent engages the second locking portion of the groove 26'. The piston 24 may then be rotated counterclockwise (relative to the housing 14) to move the detent 25 into the second locking portion of the groove 26. The pressure within the fluid pressure chamber 22 biases the piston 24 away from the housing 27 and forces frictional engagement between the detent 25 and the locking portion of the groove 26' to retain the fluid pressure within the fluid pressure reservoir 22 above ambient pressure.

The pressure and volume within the pressure reservoir 22 provided by the piston 24 should be sufficient to completely expel all the powdered medicament 12 that is loaded into the dosage chamber 32, without relying on additional deagglomerating means such as the effect of gravity. While not intending to be bound by one theory, it is believed that the flow from the pressure reservoir 22 to the medicament delivery passageway 16 may approximate flow through a nozzle or restriction such that there exists a critical pressure within the pressure reservoir 22 which will provide a maximum velocity of flow within the medicament delivery passageway 16. It is believed that any additional pressure above the critical pressure will not result in fluid velocities in the medicament delivery passageway 16 above the maximum velocity.

Generally, the higher the velocity of the fluid within a turbulence portion 50 of passageway 16, the greater the turbulence in the turbulence portion 50. The greater the turbulence, the more the dispenser 10 disperses the powdered medicament 12 into smaller, more respirable particles. The turbulence results in high shear forces on the agglomerates of medicament 12 and causes collisions between the agglomerates of powdered medicament both of which tend to deagglomerate the large agglomerates into the desired primary particles. For example, the fluid pressure chamber 22 may be pressurized to a pressure of about 74.5 pounds per square inch absolute. As an example, not intended to be limiting, an initial volume of about 1.52 cubic centimeters may be compressed to an end volume of about 0.30 cubic centimeters to provide the 74.5 pounds per square inch pressure.

For a given size of dosage chamber 32, the pressure of fluid within the fluid pressure chamber 22 sufficient to expel the powdered medicament from the dosage chamber 32 is controlled by several factors, such as the size of the pressure outlet passageway 23, the initial volume of the gas chamber 22 before pressurization and the speed with which the dosage chamber 32 is moved across the pressure outlet passageway 23. Generally, for optimal dispensing, it is believed that a user should move the dosage chamber 32 across the pressure outlet passageway 23 as fast as possible. Preferably, the entire cross sectional area of the dosage chamber 32 ultimately overlaps with the pressure outlet 23 and the total elapsed time between the time that (1) the dosage chamber 32 begins to open into the pressure outlet 23, until (2) the entire cross-sectional area of the dosage chamber 32 overlaps with the pressure outlet 23, is between about 1 millisecond and about 2 seconds, and more preferably about four milliseconds.

The pressurization assembly 20 should suddenly provide a substantial fluid pressure differential across the packed dose. To achieve this result, the pressure within the pressure chamber 22 should be at least about 1.1 times the ambient air pressure (the pressure in medicament delivery passageway 16), and preferably about twice the ambient air pressure. The volume of pressurized fluid within reservoir 22 is preferably enough to provide fluid flow during at least the time between when (1) the dosage chamber 32 begins to open into the pressure outlet 23, and (2) the entire cross-sectional area of the dosage chamber 32 overlaps the pressure outlet 23.

The dosage member 30 is mounted for movement from (1) a load position with the dosage chamber 32 generally aligned with an outlet opening 7 of the medicament reservoir 11 so that it opens into the medicament reservoir 11, to (2) a delivery or registered position with the dosage chamber 32 extending between the outlet end of the pressure outlet passageway 23 and the injection inlet end 17 of the medicament delivery passageway 16.

Preferably, in the load position, the dosage member 30 is in direct communication with the medicament reservoir 11. By direct communication, it is understood that the dosage chamber 32 is directly exposed to the reservoir without intervention of any filter, capsule, thin membrane, foil or plurality of small orifices. In this way, it is possible to more optimally compact the entire amount of the drug into the chamber 32 as the chamber 32 is in direct communication with the reservoir 11.

The actuator 40 may comprise an activation knob 44 (FIGS. 1 and 2) operatively connected to the dosage member 30 and having a knob flange 37 immovably affixed thereto. The housing 14 may have a stop flange 38 immovably affixed thereto. Rotation of the knob 44 causes the flange 37 to move relative to the stop flange 38. The stop flange 38 has surfaces adapted to abut the knob flange 37 when the dosage member 30 is moved between the load and registered positions.

At the load position (FIG. 3) the inner surfaces of the housing 14 seal the end of the dosage chamber 32 opposite the medicament reservoir opening 7, and the outer sealing surface 33 of the dosage member part 32 seals shut the outlet end of the pressure outlet passageway 23. Portions 33 of the dosage member 30 seal shut the outlet end of the pressure outlet passageway 23 during an initial part of the movement of the dosage member 30 from the load position (e.g. FIG. 3) to the registered position (e.g. FIG. 5). During a final part of the movement from the load position to the registered or delivery position, progressively increasing portions of the pressure outlet passageway 23, the dosage chamber 32, and the injection inlet 17 become aligned to afford dispersion of the dry powder medicament 12.

When (1) the dosage member 30 is positioned at the load position so that medicament 12 from the medicament reservoir 11 may be moved into the dosage chamber 32, (2) the pressurization assembly 20 is activated to pressurize fluid within the pressure reservoir 22, and (3) the dosage member 30 is then moved to the delivery position while a user is inhaling air through the air entrance passageway 19; pressurized fluid will pass from the pressure reservoir 22 through the pressure outlet passageway 23 and discharge the powdered medicament 12 from the dosage chamber 32 into the air stream being inhaled by the user through the air entrance passageway 19.

While the dosage chamber 32 has been described as moving relative to the housing 14 and the reservoir 11, it should be noted that any of the dosage member 32, medicament reservoir 11, delivery passageway 16 or the pressure outlet 23 may be mounted for movement as long as (1) in the load position or orientation, the dosage chamber 32 opens into the medicament reservoir 11, and (2) in the delivery or registered position, the dosage chamber 32 is aligned with the pressure outlet 23 and the delivery passageway 16.

FIGS. 6, 7 and 8 sequentially illustrate portions of the pressure outlet passageway 23 and the dosage chamber 32 moving into alignment. FIG. 9 illustrates the dosage chamber 32 as it initially opens into the pressure outlet passageway 23. When the dosage chamber 32 initially opens into the pressure outlet 23, a pressure differential is provided across the dose. The portion P of the dosage chamber 32 that initially opens into the pressure outlet passageway 23 and the injection inlet 17 is believed to be "blasted" from the dosage chamber 32 with the remaining powder following shortly thereafter.

The feature of the present invention wherein the pressure outlet passageway 23 is situated directly or immediately adjacent the dosage chamber 32 during dispensing of the medicament 12 is believed to contribute to complete dispersion of the medicament 12 within the dosage chamber 32. Release of the deagglomeration pressure immediately adjacent the dose and while the dosage chamber 32 moves relative to the pressure outlet 23 provides a cloud of respirable sized powdered medicament that is easily inhaled by a user, even at an inhalation airflow that is less than the rate at which an average person may inhale.

As used herein, when used to describe the release of the deagglomeration pressure, the phrase "immediately adjacent the dose" means that the dispenser is free of an obstruction or hindrance which results in a pressure drop between the position of release of the pressurized fluid and the dosage chamber or which otherwise interferes with the timely communication of the deagglomeration pressure from the pressurization assembly to the dose within the dosage chamber. Release of the deagglomeration pressure generally immediately adjacent the dose provides highly efficient use of the deagglomeration pressure as opposed to a device, for example, which includes a tortuous, labyrinth-like, or otherwise restrictive path between the release of the deagglomeration pressure and the dose, or which includes a region of ambient or otherwise unpressurized air between the release of the pressure and the dose or which include filters, membranes, capsules, small orifices, valves, sealing foils or barriers between the release of the deagglomeration pressure and the dose.

Dispensing a powdered medicament 12 in the manner according to the present invention reduces the amount of pressure required to completely dispense the powder 12. The pressurization chamber 22 need only be pressurized with enough pressurized fluid to (1) deagglomerate the powder 12, and (2) expel the medicament 12 from the dosage chamber 32 and into the medicament delivery passageway 16. The pressure within the pressurization chamber 22 preferably does not transmit all of the deagglomerated powder into the lungs of the user. Instead, preferably the user's inhalation through air entrance hole 19 (via mouthpiece 15) subsequently draws the dispersed powder completely through the medicament delivery passageway 16 and into the lungs of the user.

The pressurization assembly 20 is utilized to deagglomerate the powder within the chamber 32. The medicament delivery passageway 16 is substantially free of structure such as pallets, spirals, cups, baffles, vanes, turbulence generating channels or other structures for deagglomerating the powder beyond the deagglomeration provided by the pressurization assembly 20. Thus, the present invention does not require a user to inhale at an unduly high flow rate and reduces the surfaces that may capture and waste the medicament.

The medicament delivery passageway 16 may comprise cylindrical turbulent flow portion 50 having a generally uniform cross section that is situated adjacent the injection inlet end 17 for affording a substantially turbulent flow of fluid from the fluid pressure reservoir 22 to disperse the dry powder medicament 12 in the fluid. The medicament passageway 16 comprises a frusto-conical laminar flow portion 52 adjacent and diverging in cross sectional area toward the outlet end 18 of the medicament delivery passageway 16. The air entrance holes 19 open into the laminar flow portion 52 to afford laminar flow of fluid and dry powder medicament in the laminar flow portion 52.

The inner surface portions defining the laminar flow portion 52 preferably diverge at an angle between approximately 15 and 30 degrees with respect to each other, preferably about 22 degrees. The embodiment of dispenser 10 shown in FIGS. 1 through 12 includes four circumferentially spaced cylindrical shaped air entrance holes 19 having axes generally transverse to or normal to the axis of the medicament delivery passageway 16.

Figure 13:
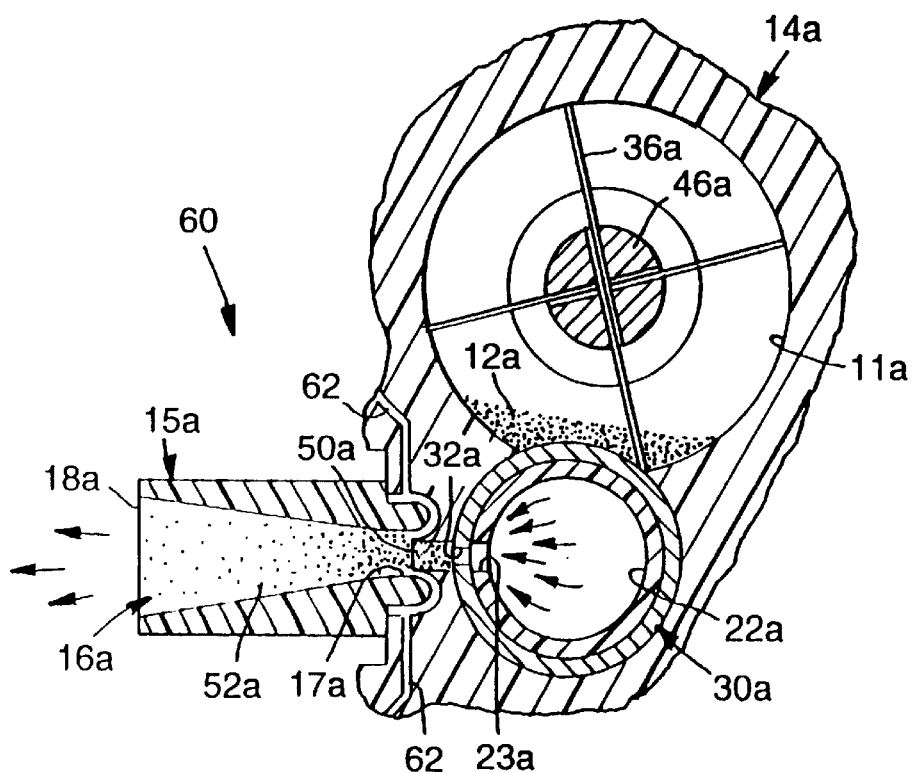
FIG. 13 is a sectional view of a modified version of the embodiment of dispenser shown in FIG. 1.

FIG. 13 illustrates a modified version of the dispenser 10 according to the present invention designated by the reference character 60 which has many parts that are essentially the same as the parts of the dispenser 10 and which have been identified by the same reference number to which the suffix "A" has been added.

Like the dispenser 10, the dispenser 60 comprises a housing 14A defining a medicament reservoir 11A for storing micronized dry powder medicament 12A, and a mouthpiece 15A having surfaces defining a medicament delivery passageway 16A having an injection inlet opening 17A and an outlet opening 18A for passage of a respirable dose of the dry powder 12A for subsequent delivery to a user. A pressure reservoir 22A and a movable dosage member 30A having chamber 32A are also provided.

Unlike the dispenser 10, the dispenser 60 includes arcuate air entrance holes or channels 62 which are positioned to afford airflow into the medicament delivery passageway 16A at an angle relative to the axis of the passageway 16A which is much less than ninety-degrees, preferably approximately zero (0) degrees. The configuration of the air entrance holes 62 shown in FIG. 13 is believed to provide a more laminar flow of air to a user.

Figure 14:
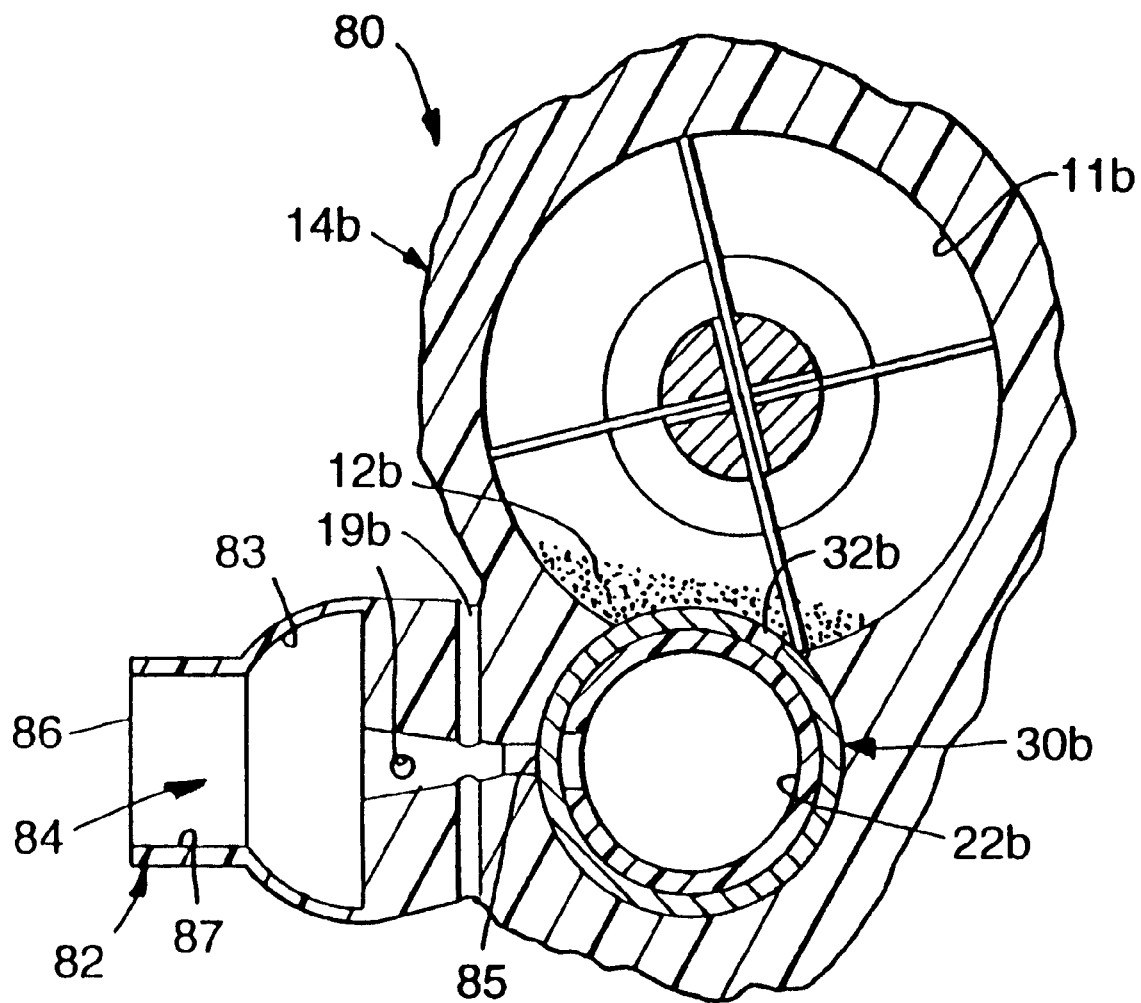
FIG. 14 is a sectional view of a modified version of the embodiment of dispenser shown in FIG. 1 which is different than the version shown in FIG. 13.

FIG. 14 illustrates another modification of the dispenser 10 according to the present invention designated by the reference character 80 which has many parts that are essentially the same as the parts of the dispenser 10 and which have been identified by the same reference number to which the suffix "B" has been added.

Like the dispenser 10 described in FIGS. 1 through 12, dispenser 80 comprises a housing 14B defining a medicament reservoir 11B for storing medicament 12B, air entrance holes 19B, a mouthpiece portion 82, a gas pressure chamber 22B and a movable dosage member 30B having a dosage chamber 32B.

Unlike the dispenser 10, the inner surfaces of the dispenser 80 include a medicament delivery passageway 84 having an injection inlet opening 85 and an outlet opening 86 for passage of a respirable dose of the dry powder 12B for described as preferably comprising three major parts A—A, B—B and C—C, alternatively the housing 114 may be comprised of fewer or additional major parts.

The housing 114 includes inner surfaces comprising a dosage member receiving chamber 109 (FIG. 24), a counter assembly receiving cavity 116 (FIG. 23), and a medicament reservoir 111. The medicament reservoir 111 has a loading aperture 101 (FIG. 23) communicating with the dosage member receiving chamber 109. For example, the medicament reservoir 111 may be semi-cylindrical shaped as shown in FIGS. 15 and 20–23 and may include an outer diameter of about 19.3 millimeters and a width of about 2.03 millimeters. A desiccant plug 106 for removing moisture from powder may be attached to intermediate portion A—A to cover an access aperture to reservoir 111. It should be noted that powder may be initially loaded into the reservoir 111 through aperture 101.

Figure 17:
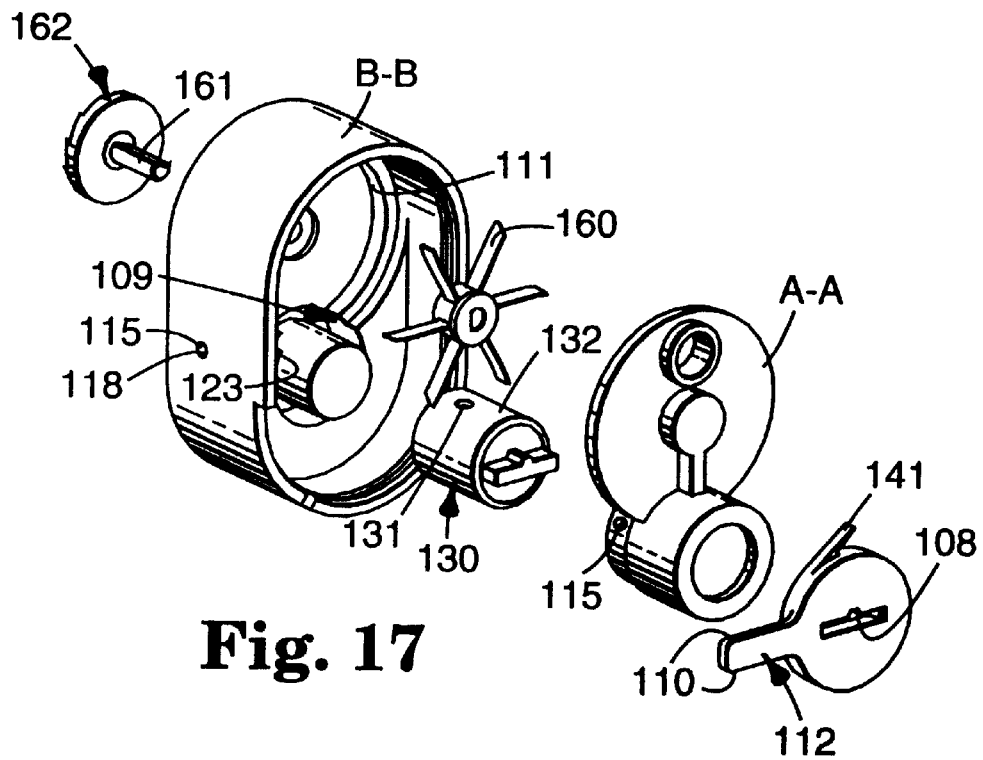
FIG. 17 is an enlarged perspective view of some of the elements of the cartridge shown in FIG. 15 taken at a different angle than that of FIG. 15 to show various details.
Figure 18:
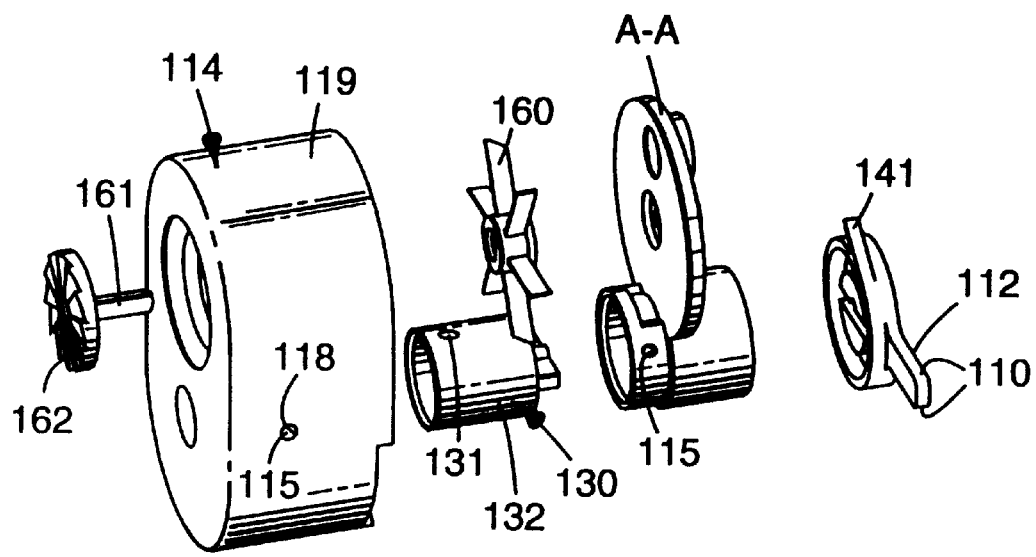
FIG. 18 is a perspective view of the elements shown in FIG. 15 taken at a different angle than that of FIG. 15 to illustrate various details.
Figure 19:
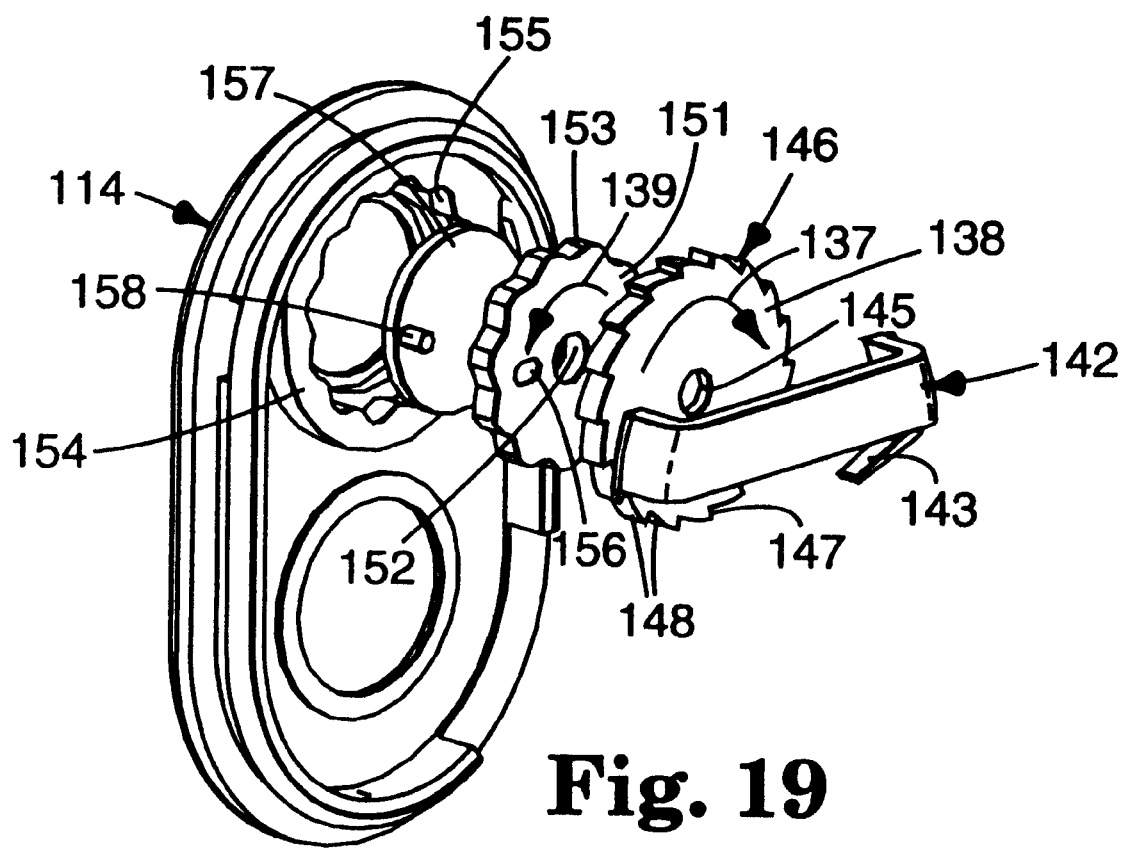
FIG. 19 is an enlarged perspective view of elements of the cartridge shown in FIG. 15 taken at a different angle to show details of portions of a counter assembly.
Figure 20:
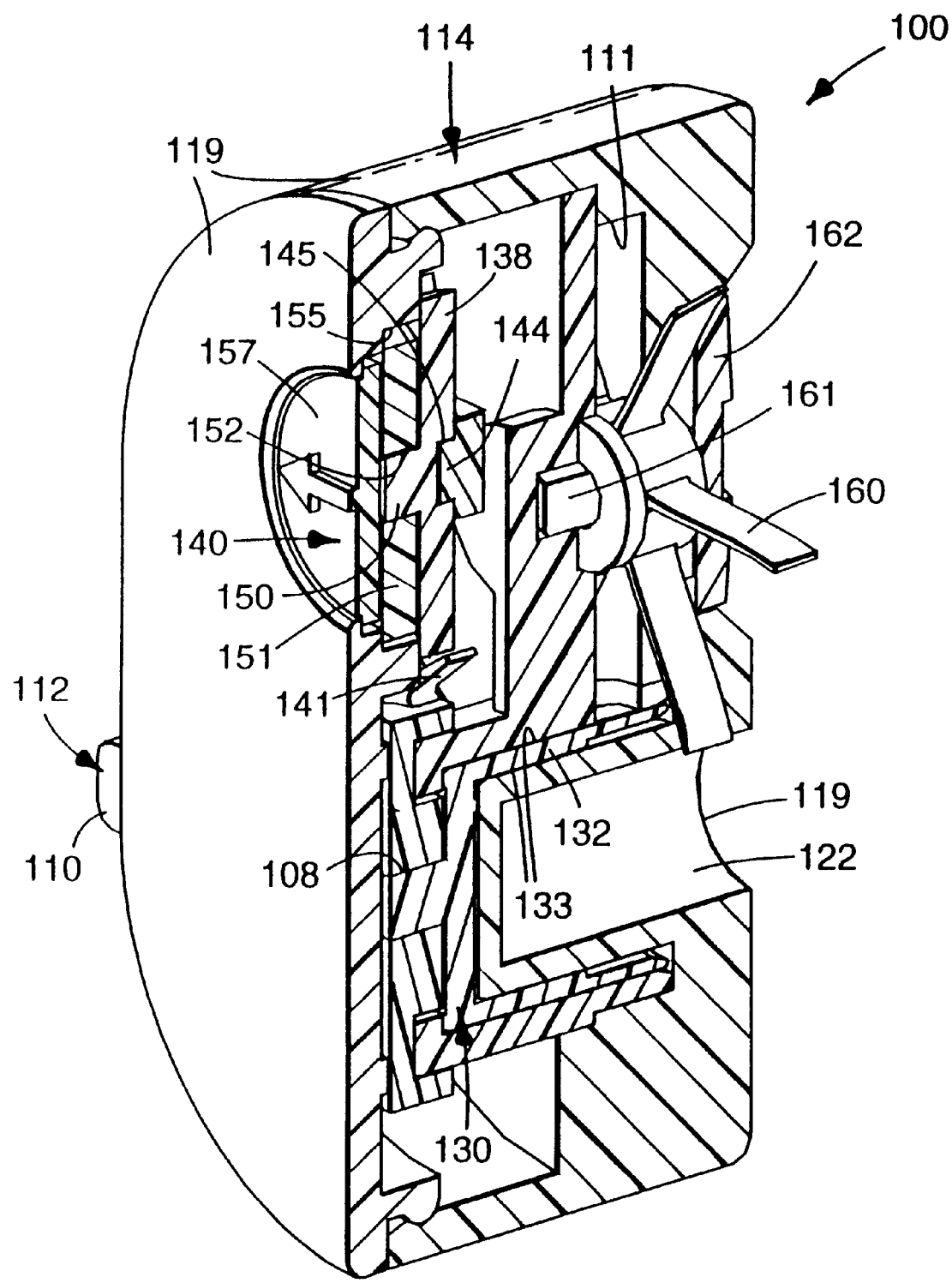
FIG. 20 is an enlarged, partial sectional, perspective view of the cartridge shown in FIG. 15 with the elements assembled.
Figure 21:
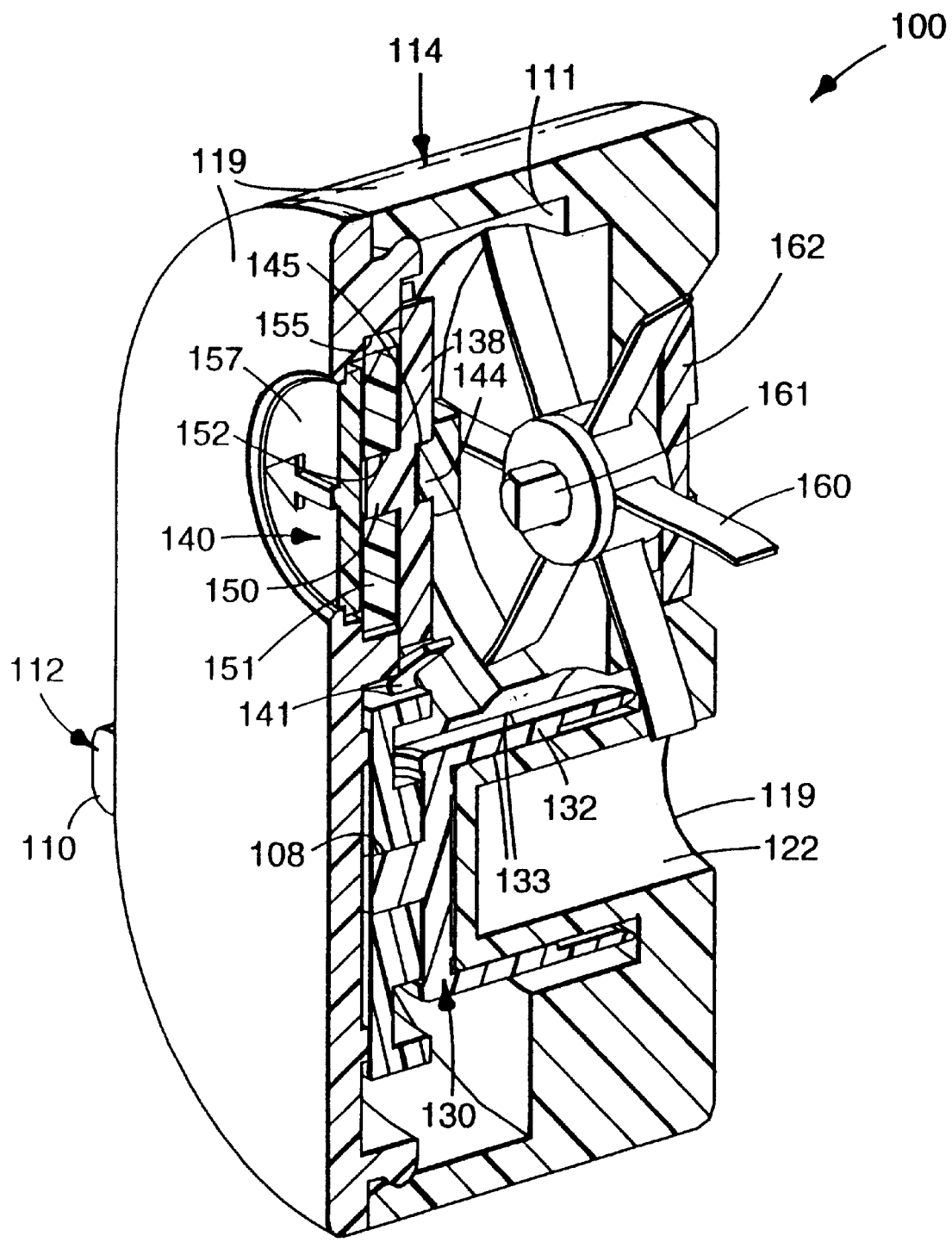
FIG. 21 is an enlarged, partial sectional, perspective view of the cartridge shown in FIG. 15 similar to FIG. 20 with parts omitted to show detail.
Figure 22:
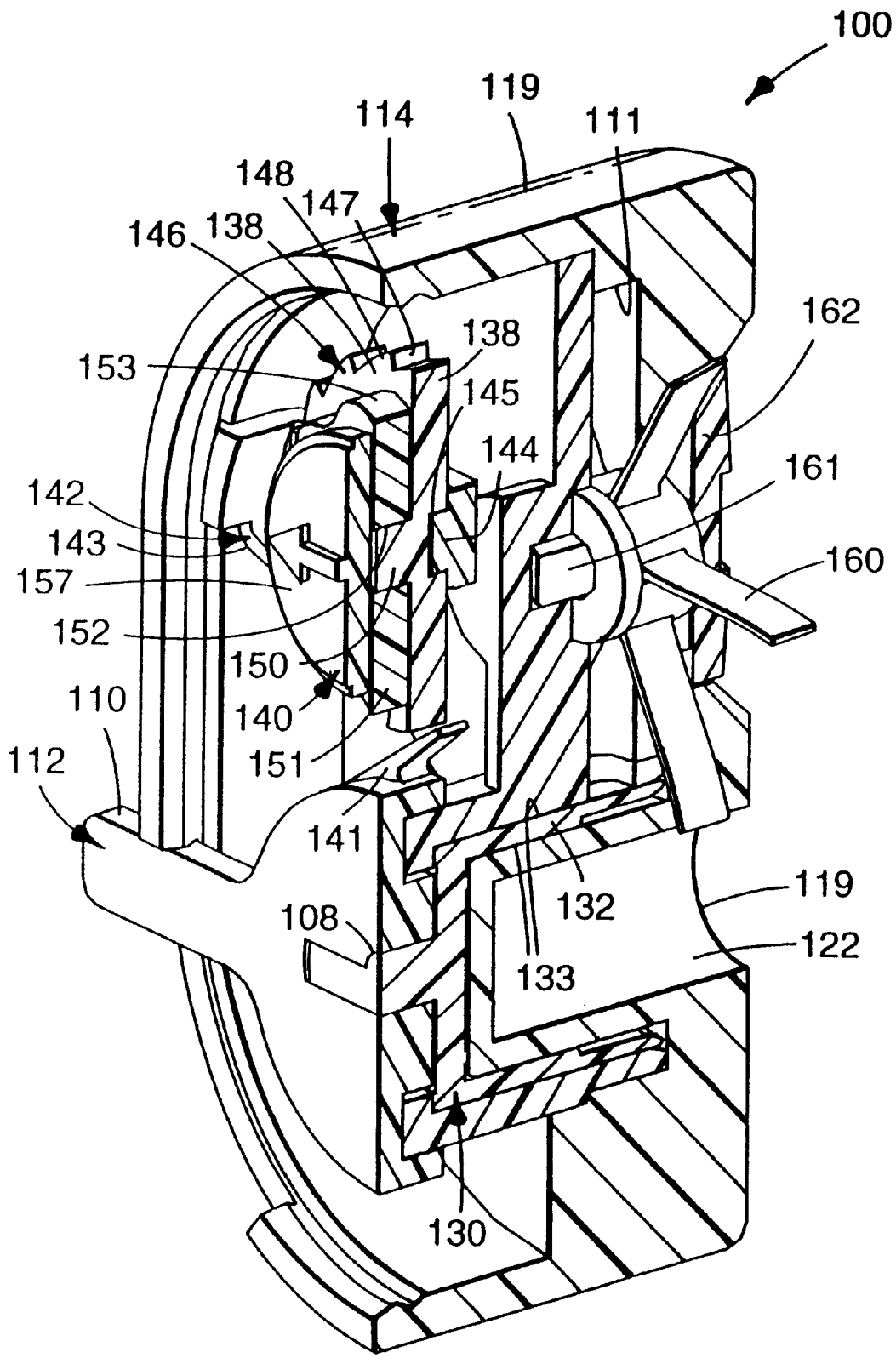
FIG. 22 is another enlarged, partial sectional, perspective view of the cartridge shown in FIG. 15 with the elements assembled and with a cover omitted to show detail.
Figure 23:
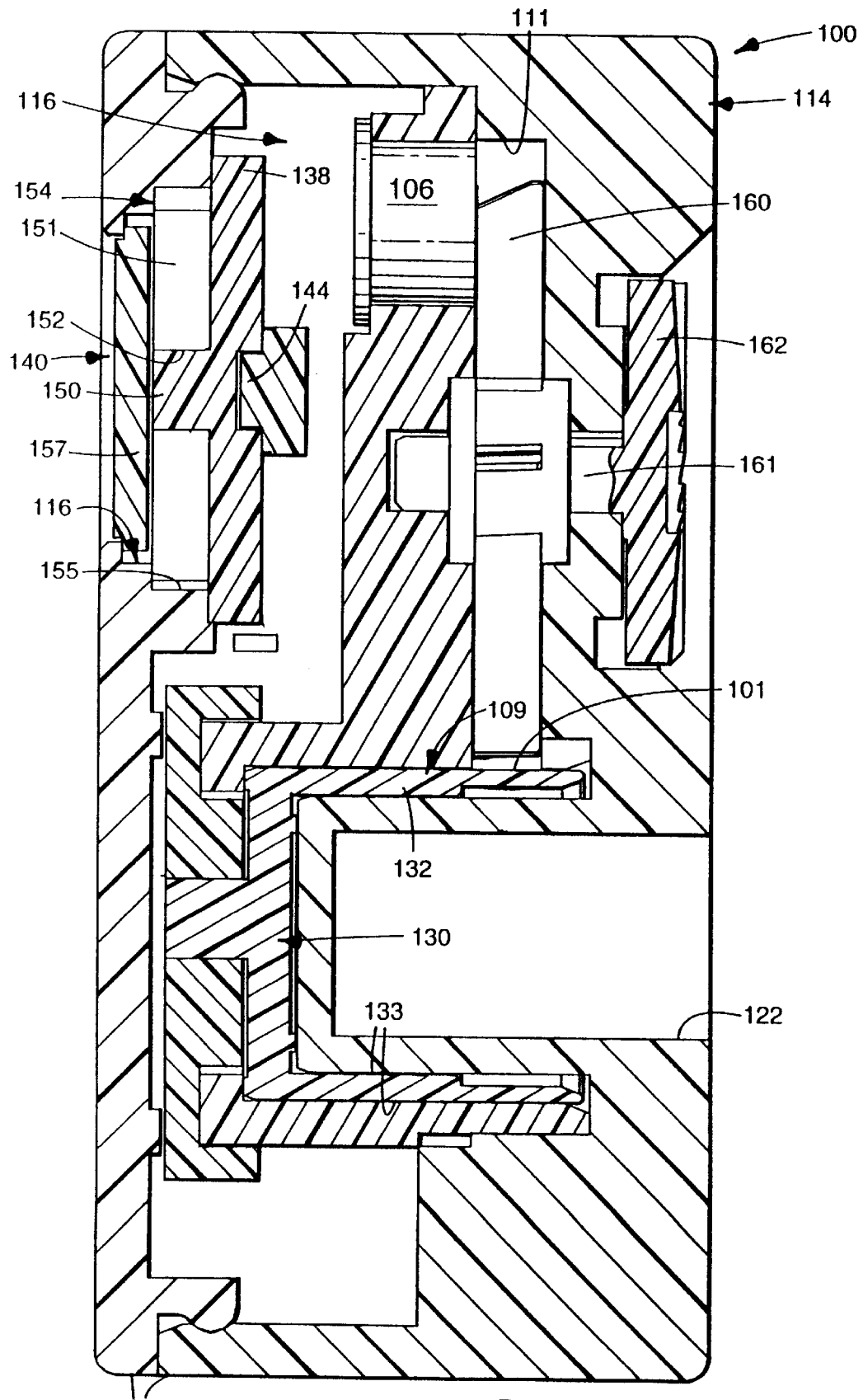
FIG. 23 is an enlarged sectional view of a cartridge assembled from the elements shown in FIG. 15 with elements broken away and omitted to illustrate various detail.

The inner surfaces of the housing 114 also include a medicament release bore 115 (e.g. a cylindrical bore having a diameter of about 1.6 millimeters and a length of about 3.2 millimeters) extending between an outlet end 118 at the cartridge housing 114 outer surfaces 119 and an injection inlet end 117. As shown in FIGS. 25 and 26, the outlet end 118 communicates with the mouthpiece portion 201 of the medicament dispenser 200. Also, as shown in FIGS. 17, 18 and 24, the medicament release bore 115 extends through portions of both major parts A—A and B—B.

Additionally, the inner surfaces of the housing 114 include portions of a pressurization assembly which includes a pressure reservoir or chamber 122 (e.g. a cylindrical chamber having a diameter of the inner surfaces of the chamber of approximately 5.82 millimeters) that opens to the outer surfaces 119 of the housing 114. The pressure reservoir 122 is operatively connected to a pressurization member 211 of the pressurization assembly by, for example, a suitable sealing means (e.g. an elastomeric or rubber ring or washer, not shown) press fit between the housing 114 and the dispenser 200. The pressure reservoir 122 is pressurized by the pressurization member 211 of the medicament dispenser 200. For example, the pressurization member 211 may comprise a piston/cylinder arrangement.

Figure 24:
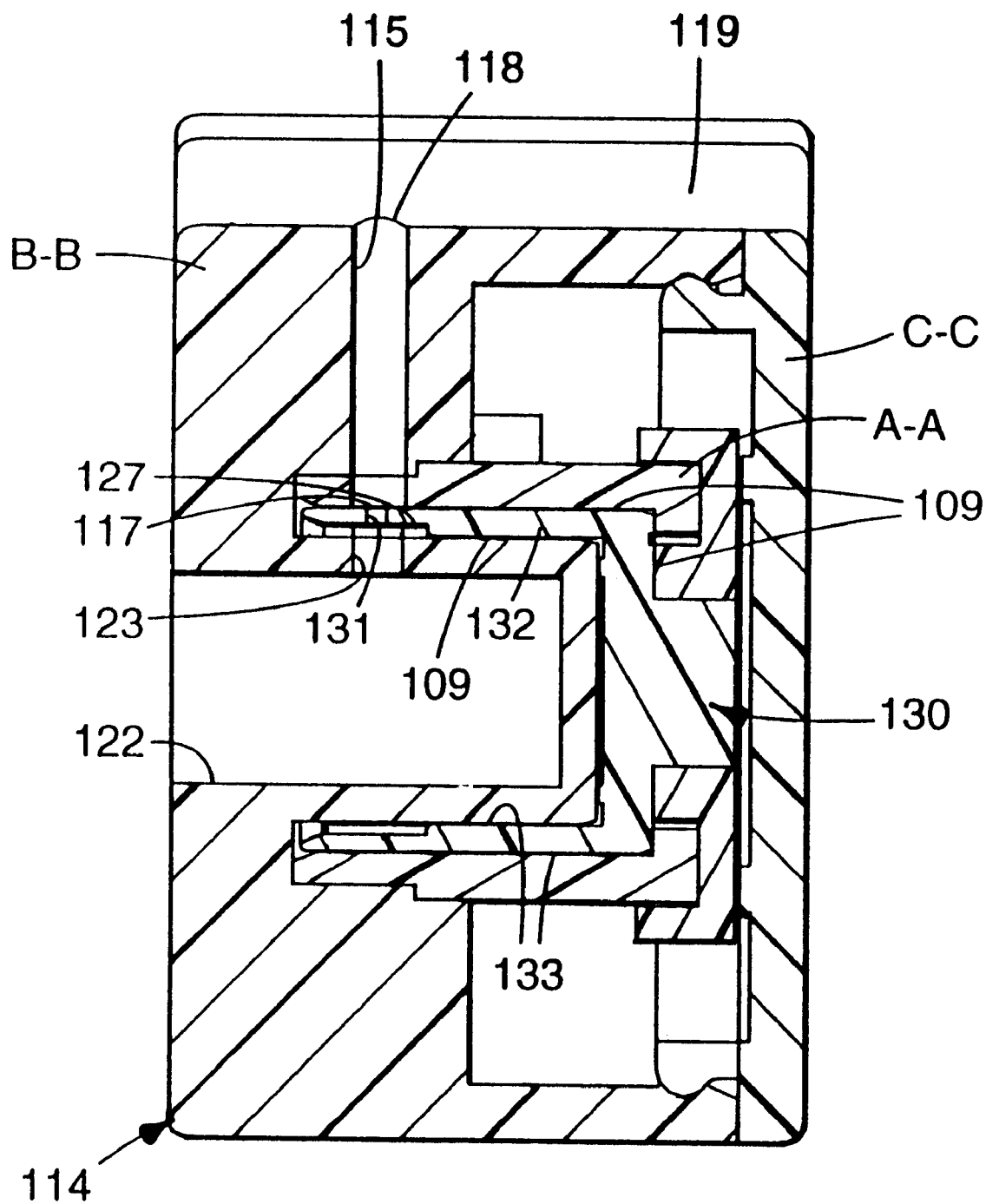
FIG. 24 is an enlarged sectional view of a cartridge assembled from the elements shown in FIG. 15 and including a sealing element between a metering sleeve and a pressure chamber.

FIG. 24 illustrates that the inner surfaces of the housing 114 include a pressure release bore or outlet 123 (e.g. a cylindrical bore having a diameter of about 1.6 millimeters and having a length of about 1.01 millimeters) having a first end communicating with the pressure reservoir 122 and a second end opening through the inner surface defining the dosage member receiving chamber 109 generally opposite the injection inlet end 117 of the medicament release bore 115.

The cartridge 100 includes a dosage member 130 mounted within the dosage member receiving chamber 109. The dosage member 130 includes a cylindrical, tubular dosage part 132 having sealing surfaces 133 and having a dosage chamber 131 extending through the dosage part 132 between spaced parts of the sealing surfaces 133. The dosage member 130 may be constructed of a material similar to the material used to construct the dosage member 30. As an example not intended to be limiting, the dosage member 130 may comprise a sleeve with dimensions similar to those given in the example of the dosage member 30 described above. The cross-section of the dosage chamber 131 may vary similar to the cross-section of the dosage chamber 32 mentioned above.

Figure 15:
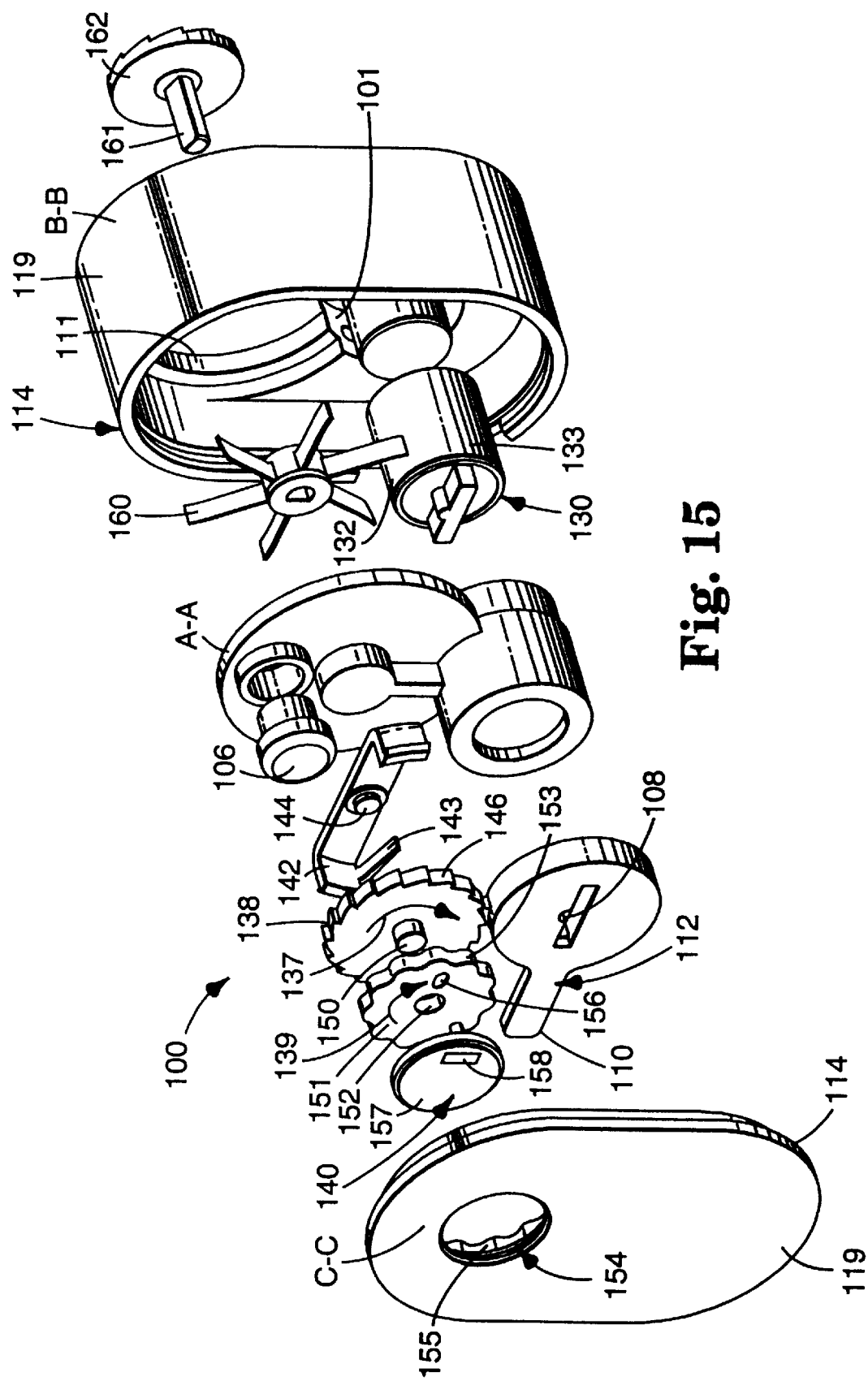
FIG. 15 is an exploded perspective view of a cartridge according to another aspect of the present invention.

FIG. 24 illustrates a sealing means added to the elements of the cartridge 100 shown in FIG. 15. The sealing means comprises, for example, a biasing rubber or elastomeric member 127 attached between the dosage member 130 and the pressure release bore 123/pressure reservoir 122 to provide a seal between the pressure release bore 123/pressure reservoir 122 and the dosage member 130. The sealing means 127 may be simultaneously injection molded with the remaining portions of the pressure reservoir 122 portion of the housing or may be adhered thereto with an appropriate adhesive. As shown in FIG. 24, the sealing means 127 includes a bore extending therethrough so that the dosage chamber 131 and medicament release bore 115 communicate with the pressure release bore 123.

The cartridge 100 also includes an actuation arm 112 connected to the dosage part 132. The actuation arm has portions extending beyond the outer surfaces 119 of the cartridge housing 114. The actuation arm 112 includes surfaces 110 adapted to be manipulated by an actuator and transmission of the medicament dispenser 200. The actuation arm 112 may be connected to the dosage member in any suitable manner such as by a snap fit with a detent groove 108 to afford proper orientation of the arm 112 relative to the dosage member 130.

The actuation arm 112 moves the dosage member 130 from (1) a load position (e.g. FIG. 26) with the dosage chamber 131 opening into the loading aperture of the medicament reservoir 111, to (2) a registered or delivery position (FIG. 25). The movement between the load and delivery positions of the dosage member 130 relative to the reservoir 111, injection inlet 117 and the pressure release bore 123, is similar to the movement between the load and delivery positions of the dosage member 30 relative to the reservoir 11, gas pressure release aperture 23 and the injection inlet 17 of the dispenser 10 shown in FIGS. 3, 5 and 6 through 9.

In summary, when (1) the dosage member 130 is positioned at the load position so that powdered medicament from the medicament reservoir 111 may be flowed into the dosage chamber 131, (2) the pressure chamber is pressurized, and (3) the dosage member 130 is then moved from a position spaced from the registered position to the registered position, pressurized gas will pass from the pressure reservoir 122 through the pressure release bore 123 and discharge the powdered medicament from the dosage chamber 131 into the medicament release bore 115.

The cartridge assembly 100 may optionally include a counter assembly 140 mounted within the counter assembly receiving cavity 116 for calculating the number of times the actuation arm 112 moves the dosage member 130 from the load position to the registered position and back to the load position. Such a calculation affords an estimate of the number of dosages of medicament remaining in the medicament reservoir 111.

The counter assembly 140 comprises the actuation arm 112 having a counter assembly drive rod 141, the cartridge housing 114 having indicating means such as numerals (not shown) on its outer surfaces, a restraining assembly 142 comprising a leaf pawl 143 mounted within the counter assembly receiving cavity 116.

The counter assembly includes the cartridge housing 114 having a ratchet wheel hub 144 (e.g. disposed on the restraining assembly 142), a ratchet wheel 138 having an axis, axially centered hub bearing surfaces 145, and a plurality of teeth 146 at its periphery. The ratchet wheel 138 preferably has a diameter of about 13.41 millimeters.

Each of the teeth 146 have a shoulder surface 147 and a release surface 148. The ratchet wheel bearing surfaces 145 are journaled on the ratchet wheel hub 144, and the ratchet wheel 138 is mounted within the counter assembly receiving cavity 116 for rotation relative to the cartridge housing 114. When the dosage member 130 moves from the registered position to the load position, the drive rod 141 engages a shoulder surface 147 of a ratchet wheel tooth 146 to sequentially move the ratchet wheel 138 in a first rotational direction 137 (FIG. 15) relative to the cartridge housing 114 to record the delivery of a dose of medicament, and engagement between the leaf pawl 143 and a shoulder surface 147 of a ratchet wheel tooth 146 arrests movement of the rachet wheel 138 relative to the cartridge housing 114 in a direction opposite to the first rotational direction 137 when the drive rod 141 moves out of engagement with the shoulder surface 147 and along a release surface 148 of another ratchet wheel tooth 146 when the dosage member 130 moves from the load to the delivery position.

The counter assembly 140 may comprise only the rachet wheel 138 described above, when, for example there are only a few dosages of medicament within the reservoir 111. In this example, the ratchet wheel 138 includes indicia such as an arrow (not shown) thereon for cooperating with the numerals (not shown) on the outer surface 119 of the housing to calculate the number of times the actuation arm 112 moves the dosage member 130 from the load position to the registered position and back to the load position. However, preferably the counter assembly further comprises reduction means, particularly when the medicament reservoir 111 holds a large number of dosages (e.g. over 25).

The following described reduction means is believed to afford counting of up to about 210 dosages of medicament. The reduction means comprises the ratchet wheel 138 having an axially offset drive rib 150, an eccentric orbital gear 151 having an axis and bearing surfaces 152 for receiving the drive rib 150, and radially outwardly extending gear teeth 153. For example, the ratchet wheel 138 is constructed from any suitable material such as a polycarbonate, acetal or an acetate. The ratchet wheel may be constructed from ULTEM™ and have a pitch diameter of about 0.211 inches.

The reduction means also comprises the inner surfaces of the cartridge housing 114 having an annulus 154 (FIG. 14) including an annulus axis, and radially inwardly extending gear teeth 155 for engaging the gear teeth 153 of the eccentric orbital gear 151. For example, the pitch diameter of the annulus 154 is approximately 0.23 inches.

Figure 16:
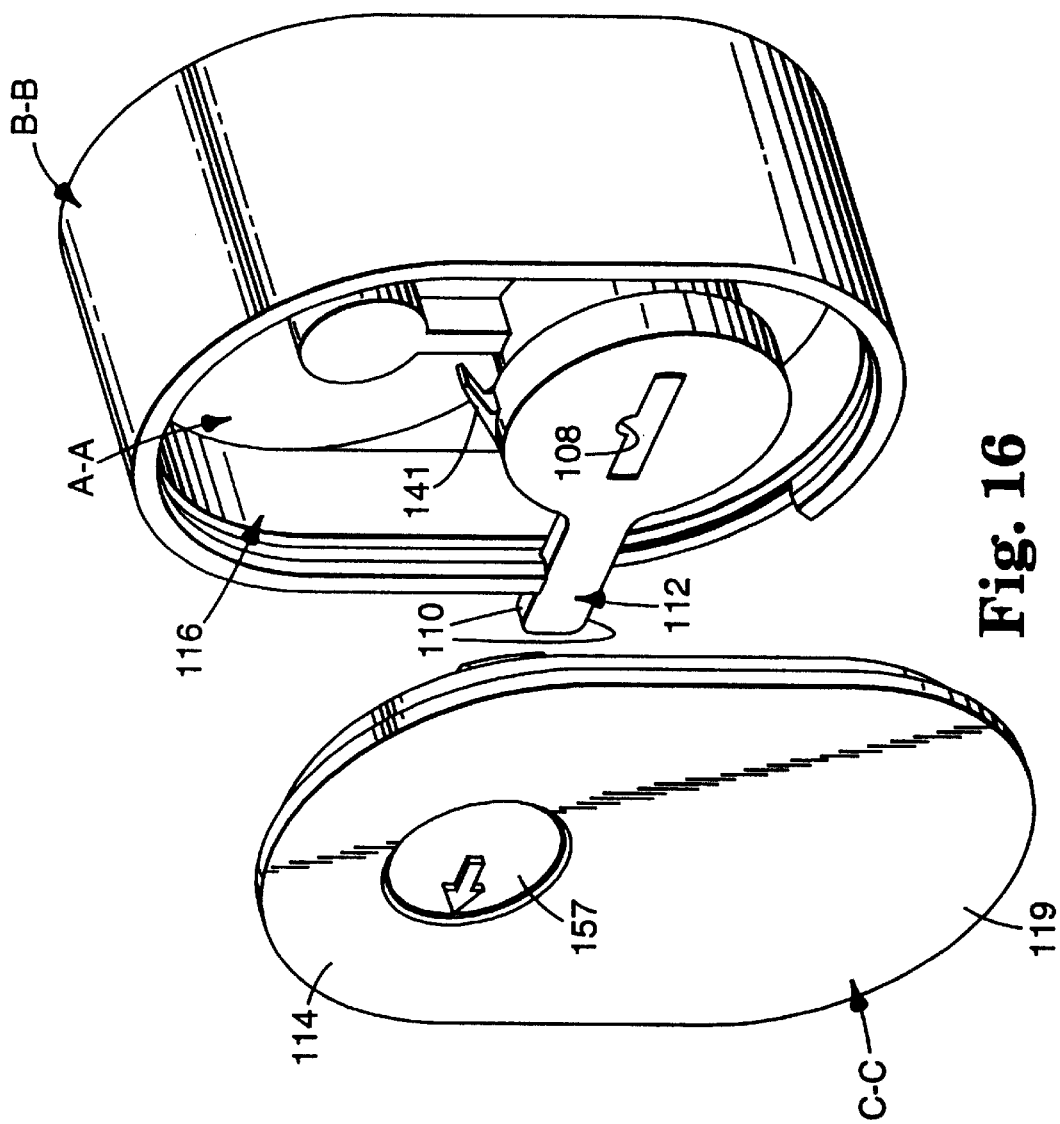
FIG. 16 is an enlarged perspective view of a partially assembled cartridge using some of the elements shown in FIG. 15.

When the ratchet wheel 138 is driven in the first direction 137, the eccentric orbital gear teeth 153 engage the annulus gear teeth 155, and the eccentric orbital gear 151 moves in a second rotational direction 139 (FIG. 15) generally opposite the first rotational direction 137. Optionally, the reduction means further includes the eccentric orbital gear 151 having axially offset drive bearing slot surfaces 156, and a cover plate 157 having indicating indicia means (e.g. the arrow shown in FIGS. 15 and 16) thereon, and a drive finger 158 received in the bearing slot surfaces 156 of the eccentric orbital gear 151. In operation, when the eccentric orbital gear 151 moves relative to the annulus 154, the bearing slot surfaces 156 move the cover plate 157 in generally the second rotational direction 139 to thereby move the indicating indicia means (e.g. the arrow) on the cover plate 157 relative to the indicating means (e.g. the numerals, not shown) on the outer surfaces 119 of the cartridge housing 114.

The bearing slot surfaces 156 are larger than the drive finger 158, and the drive finger may move within the slot surfaces 156. Thus, the cover plate 157 translates the eccentric motion of the eccentric orbital gear 151 into increments of generally circular motion so that the indicia means (e.g. the arrow) rotates in a defined, aesthetically pleasing circular path relative to the indicating means (e.g. the numerals) on the outer surfaces 119 of the cartridge housing 114.

The cartridge 100 also includes a powder loading assembly similar to the powder loading assembly for the dispenser 10 described above. The cartridge 100 and powder loading assembly afford storage of powdered medicament 12 in a reservoir 111 that (1) may be stirred or agitated after the cartridge 100 is delivered to the ultimate user, and (2) may be stored remote from the dispenser 200 prior to its use.

The powder loading assembly comprises flexible blades 160 having proximal and distal ends. Like the blade 32 of the dispenser 10, the blade 160 separates agglomerates of the dry powder medicament 12 into smaller agglomerates and separates the dry powder from walls of the medicament reservoir 111.

The powder loading assembly also includes a blade shaft 161 connected to the blade 160, and a one-way gear clutch 162 connected to the blade shaft 161 and adapted to be engaged by portions of a transmission assembly of the medicament dispenser 200. For example, the transmission assembly of the medicament dispenser 200 may include a complementary spring loaded gear clutch 275 which engages the one-way gear clutch 162 to drive the blade(s) 160 in a predetermined powder loading direction, and which releases from the one-way gear clutch 162 when the spring loaded gear clutch 275 is rotated in a direction opposite the powder loading direction.

Also, like the blade 36 in the dispenser 10, when the blade 160 in cartridge 100 is mounted within the medicament reservoir and is driven by the transmission assembly of the medicament dispenser 200, the blade 160 moves along first and second predetermined paths within the medicament reservoir 111. During a first part of the predetermined path, the leading surface of the blade 160 leads and the distal end of the blade 160 moves along a portion of the inner surface defining the medicament reservoir 111. During a second portion of the predetermined path, the distal end of the blade 160 moves along and contacts a portion of the outer sealing surface 133 of the dosage member 130 (or a thin layer of powder adjacent thereto) and bends generally in the manner described above.

Operation of the Cartridge

The operation of the cartridge according to the present invention will now be described with reference to the preferred embodiment 100 and with reference to an example of a dispenser 200. FIGS. 25 and 26 sequentially illustrate the operation of the cartridge 100 in conjunction with the dispenser 200.

The cartridge 100 shown in FIGS. 25 and 26 is generally identical to the cartridge 100 shown in FIGS. 15 through 24 except that the position of the actuation arm 112 in the load and registered positions is generally lower in FIGS. 25 and 26 than the position of the actuation arm 112 in FIGS. 15 through 24. The actuation arm 112 is shown in this manner to better illustrate the operation of the transmission and actuator of the dispenser 200.

The cartridge 100 is received in the dispenser 200 which includes a housing 202 including a mouthpiece portion 201, pressurization member 211, and portions of a transmission assembly and actuator. The actuator and transmission are preferably mechanical assemblies which minimize or reduce the inputs or operations required from a user. However, it should be noted that the actuator and transmission may comprise a variety of different structures ranging from a strictly manual actuator and transmission to a completely automatic actuator and transmission.

The actuator and transmission include a cammed fork member 204 (shown in FIGS. 25 and 26 by dashed lines) having surfaces 206 for receiving the manipulation surfaces 110 of the actuation arm 112. The cammed fork member 204 is pivotally mounted on the housing 202 of the dispenser 200 to move between load (FIG. 26) and registered (FIG. 25) positions corresponding to the positions of the actuation arm 112.

The transmission includes rack 220 and gear 221 assemblies. The rack 220 includes a button member or handle 219 that is manually slidable within guide surfaces of housing 202 between an "armed" position shown in FIG. 26 and a release position shown in FIG. 25. When the handle 219 is slid to the armed position, the gear 221 rotates clockwise in the drawing and causes a piston member 211 to compress fluid (e.g. air) within the pressure reservoir 122 of the cartridge similar to the manner in which the pressure reservoir 22 is pressurized. Alternatively, the rack 220/handle 219 may be replaced with a circular gear (not shown) connected to and driven by a pivotal mouthpiece cover (not shown).

Clockwise rotation of the gear 221 in FIG. 25 rotates spring drive clutch 275. Spring drive clutch 275 engages one-way gear clutch 162 to drive the blades 160 within the medicament reservoir 111 in a predetermined powder loading direction. The spring drive clutch 275 releases from the one way gear clutch 162 (and thus does not drive the one-way gear clutch 162) when the gear 221 rotates counterclockwise in FIG. 25. Alternatively, an intervening gear (not shown) may be placed between gear 221 and gear 275 to control the direction of rotation of the spring drive clutch 275.

At generally the same time that the handle 219 is slid to the armed position, a linkage 225 causes the cammed fork member 204 to pivot about its pivot point on housing 202 against the bias of firing spring 226. The linkage 225 will cause the cammed fork member 204 to pivot clockwise in FIGS. 25 and 26 until just after the fork member 204 engages cam surfaces 231 on latch member 230. The latch member 230 comprises a portion of the actuator of the dispenser 200 and includes a means for releasably retaining the dosage chamber 131 spaced from the registered position against the bias of the spring 226.

The latch member 230 is pivotally mounted on the housing 202 for movement between a latched and release position. The latch member 230 includes a latching spring 235 for biasing the latch member 230 toward the latched position, and a release button 238 for manually pivoting the latch member 230 against the bias of the spring 235.

When the cammed fork member 204 engages cam surfaces 231 (such as when the transmission returns the dosage chamber 131 to the load position), the latch member 230 pivots against the bias of spring 235 out of the path of the cammed fork member 204 until a trailing edge of the cammed fork member 204 clears the cam surfaces 231. The cammed fork member 204 engages shoulder surfaces 239 of latch 230 to releasably retain the dosage chamber in the load position. This is the position of the cammed fork member 204 and the latch 230 shown in FIG. 26.

The linkage 225 causes the actuation arm 112 to move from the registered to the load position before the handle 219 moves completely to the armed position. During a final portion of the movement of the handle 219 to the armed position, the actuation arm 112 will be in the delivery position and the spring drive clutch 275 will cause the blades 160 to load the dosage chamber 131 with medicament.

After the dosage chamber 131 is loaded with a dosage of medicament and after the actuation arm 112/cammed fork member 204 is in the position shown in FIG. 26, the dispenser is ready for actuation. To actuate the dispenser 200, a user manually presses on the button 238 which releases cammed fork member 204 which is under the bias of spring 226. The spring 226 moves the cammed fork member 204 from the load to the registered position and consequently the actuation arm 112 from the load to the registered position. It should be noted that the latch member 230 need not include a button member but may instead comprise an inhalation activated means such as the inhalation activated mechanisms shown in U.S. Pat. Nos. 5,069,204; 4,664,107; and those mentioned in 4,664,107 including 3,187,748; 3,456,644; 3,645,645; 3,456,646; 3,565,070; 3,598,294; 3,814,297; 3,605,738; 3,732,864; 3,636,949; 3,789,843 and 3,187,748 or the inhalation activated assembly described below.

Referring now to FIG. 26, the linkage 225 comprises a slider member at its distal end. The linkage 225 may be constructed to move the gear 221 and the handle 219 back to the position shown in FIG. 25 after the button 238 is pressed. Alternatively, the linkage 225 may be constructed to release after the button 238 is pressed. In that alternative, the user manually moves the handle 219 from the position shown in FIG. 26 to the position shown in FIG. 25 after the cartridge 100 is fired.

Referring now to FIGS. 27 through 35, there is shown another dispenser according to the present invention generally designated by reference character 300.

Figure 27:
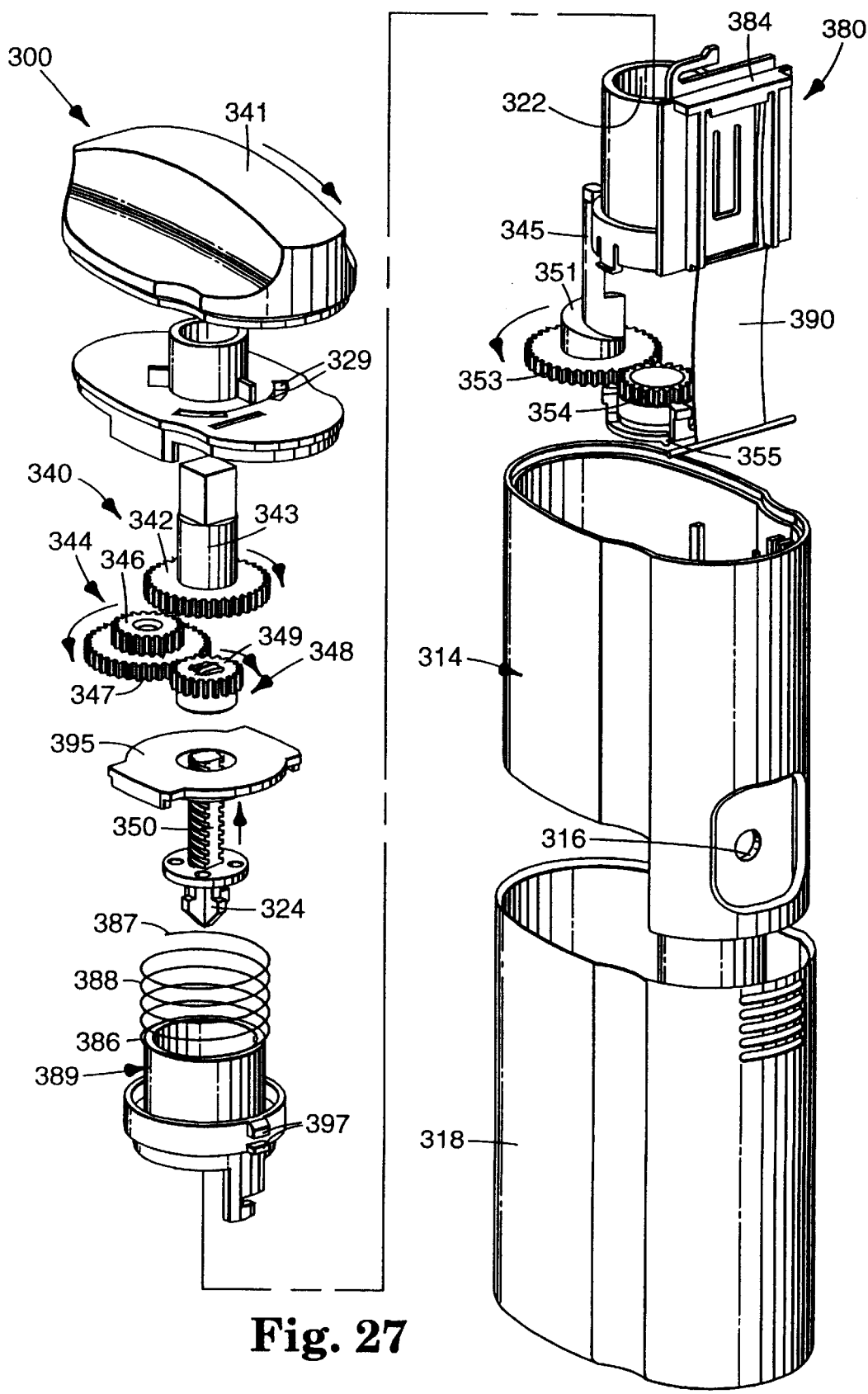
FIG. 27 is an exploded perspective view of elements of a fourth aspect of dry powder dispenser according to the present invention which (1) has a cartridge portion omitted to illustrate details; (2) optionally utilizes an inhalation activated assembly of the present invention, and (3) includes a novel transmission assembly.
Figure 28:
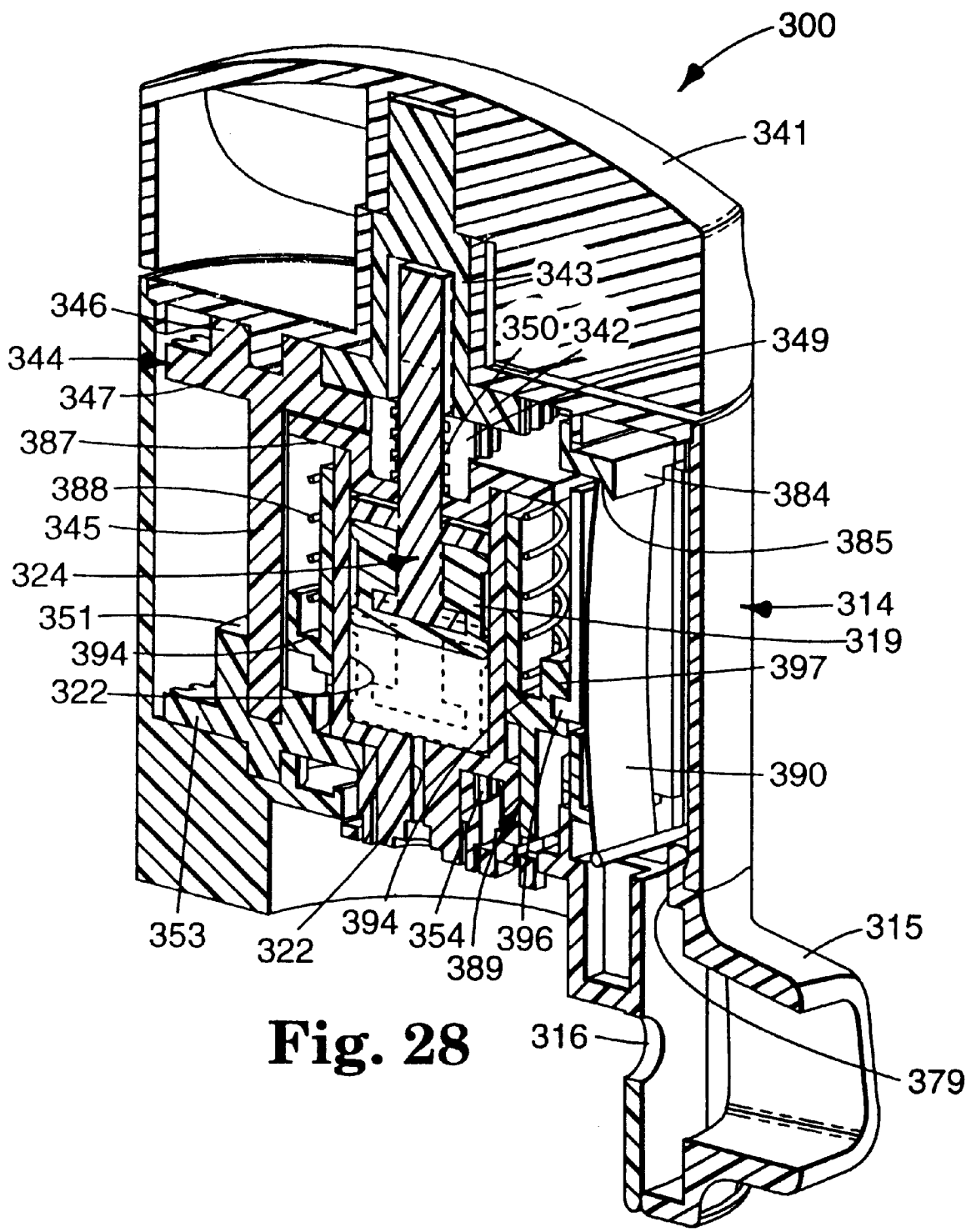
FIG. 28 is a sectional, perspective view of the assembled elements of FIG. 27 except that a mouthpiece portion has been added to the housing of the dispenser and various features have been omitted to illustrate details.
Figure 29:
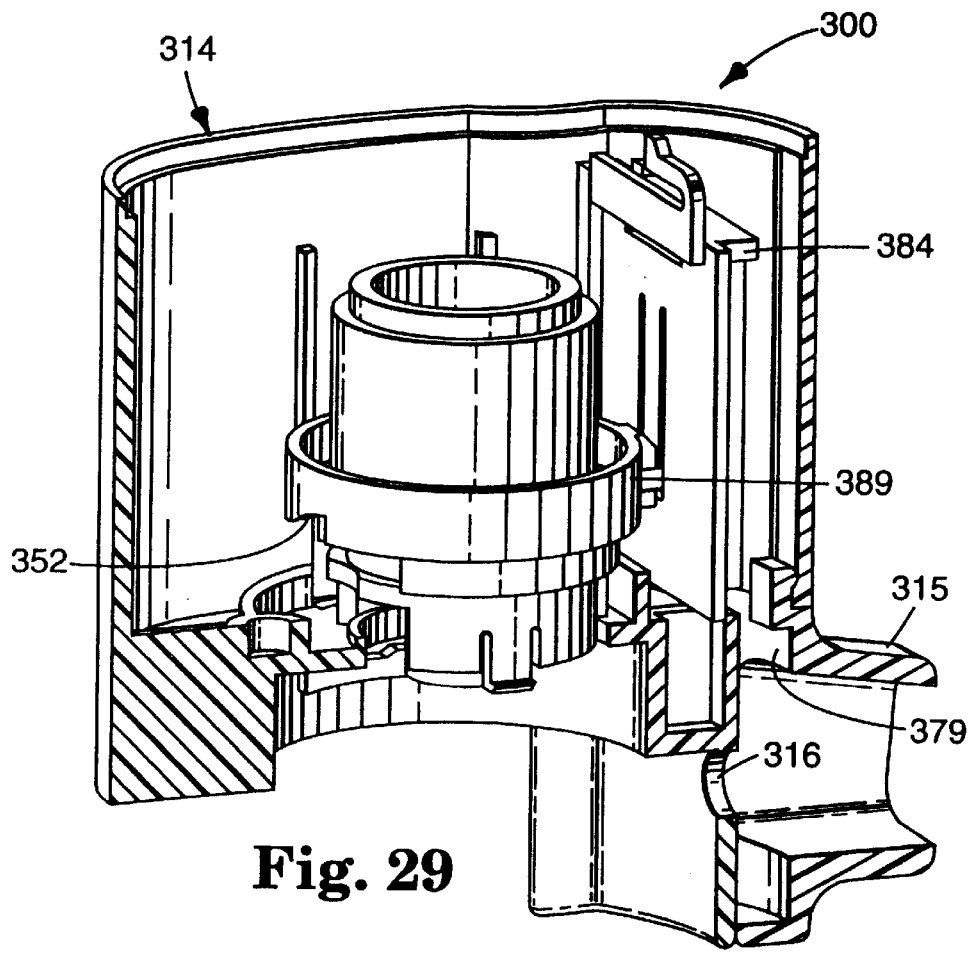
FIG. 29 is a partial sectional perspective view of various assembled elements shown in FIG. 27 which illustrates the location of a pressure reservoir in the dispenser.
Figure 30:
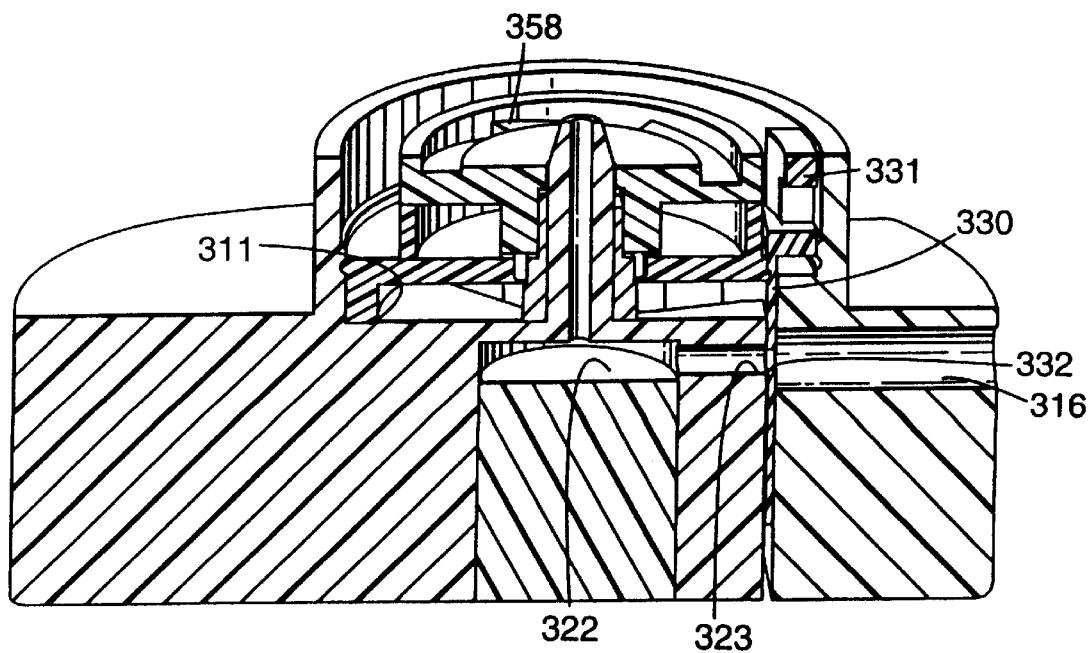
FIG. 30 is an enlarged sectional perspective view of a cartridge for use with the dispenser elements illustrated in FIG. 27.
Figure 31:
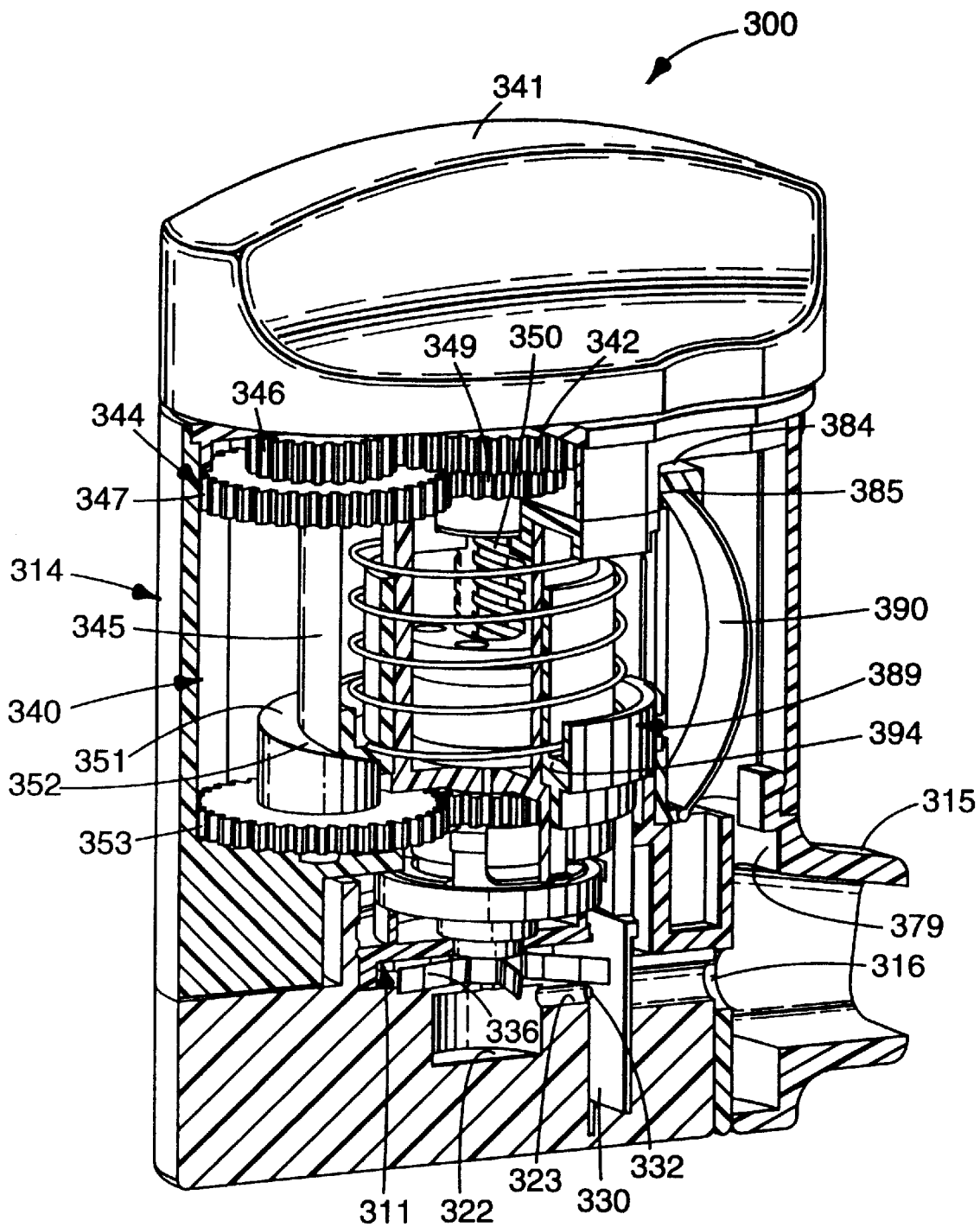
FIG. 31 is a partial sectional, partial perspective view of the cartridge of FIG. 30 assembled with the elements shown in FIG. 27 and including a mouthpiece portion.
Figure 32:
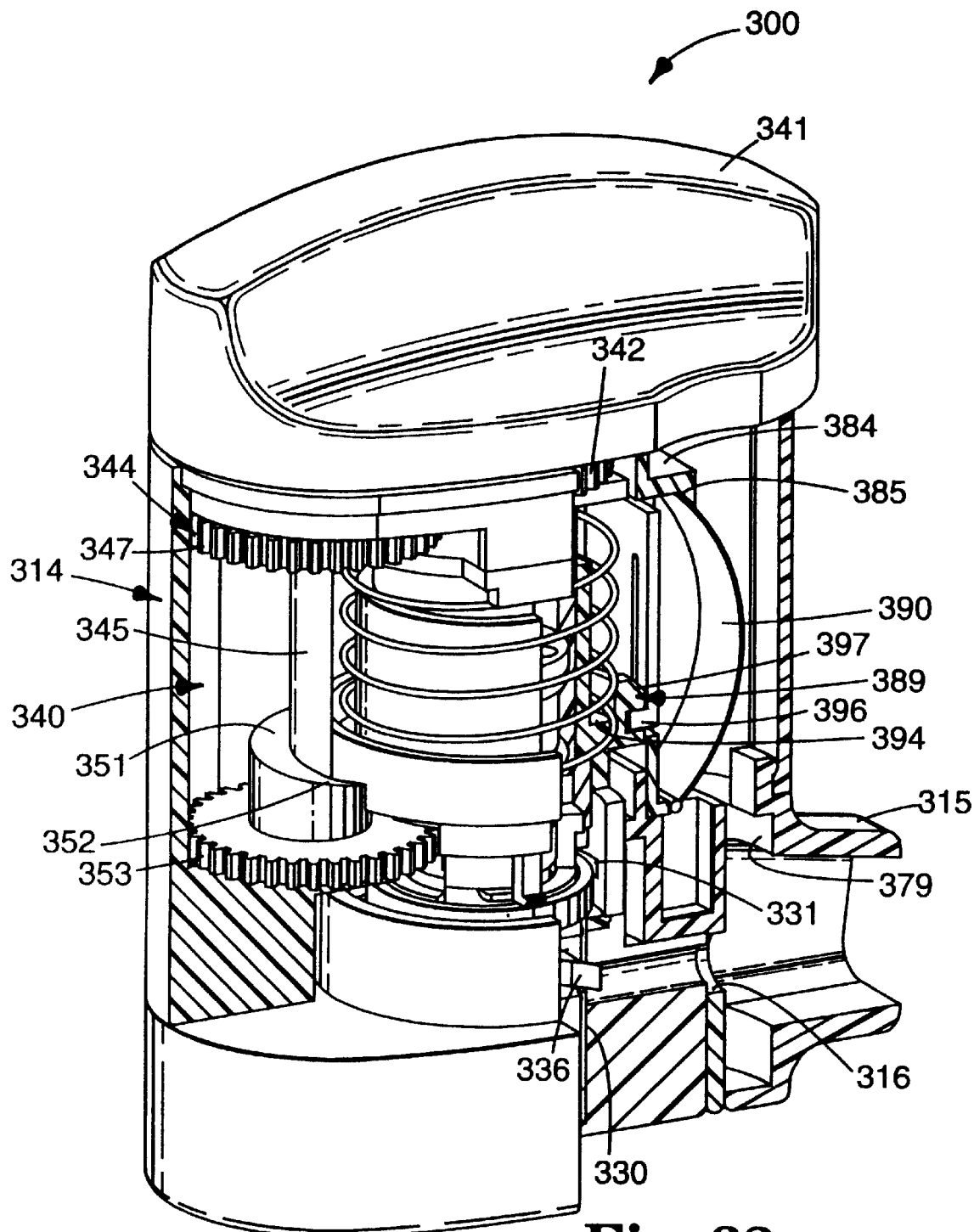
FIG. 32 is a partial sectional, perspective view similar to FIG. 31, taken from a slightly different perspective angle than FIG. 31.

The dispenser 300 includes a housing 314 having outer surfaces which enable a user to grasp the dispenser 300. FIG. 27 illustrates an optional cover which may be used to protect the dispenser 300. The cover 318 may be slid over a housing 314 of the dispenser 300. Alternatively, the dispenser 300 may include mouthpiece portion 315 as shown in FIGS. 28 and 29 which would utilize a cover different than the cover 318.

Preferably, like the dispenser shown in FIGS. 25 and 26, the dispenser 300 includes base (FIG. 27) and cartridge (FIG. 30) assemblies, although alternatively the dispenser may comprise a single, integral unit. The dispenser 300 has actuator and transmission assemblies which are different than those described in FIGS. 25 and 26. The actuator and transmission assemblies of the dispenser 300 are described below.

The cartridge assembly is best seen in FIGS. 30–33 and comprises a medicament reservoir 311 for holding a bulk supply of micronized powder medicament, a dosage member 330 having a dosage chamber 332 for releasably containing a predetermined, agglomerated dose of the medicament, and an agglomerator (e.g. blades) 336 for transferring a quantity of the dry powder medicament from the medicament reservoir 311 to the dosage chamber 332 and for packing the quantity into the predetermined, agglomerated dose within the dosage chamber 332.

As an example, not intended to be limiting, the medicament reservoir 311 may have a diameter of about 0.75 inches, and a thickness of about 0.100 inches. The blades 336 may be constructed from any suitable high modulus material such as acetol, nylon, polycarbonate or polyester. Preferably the blades 336 are injected molded using grade 1010F ULTEM™ generally available from General Electric Plastics Sales of Selkirk, N.Y.

Figure 36:
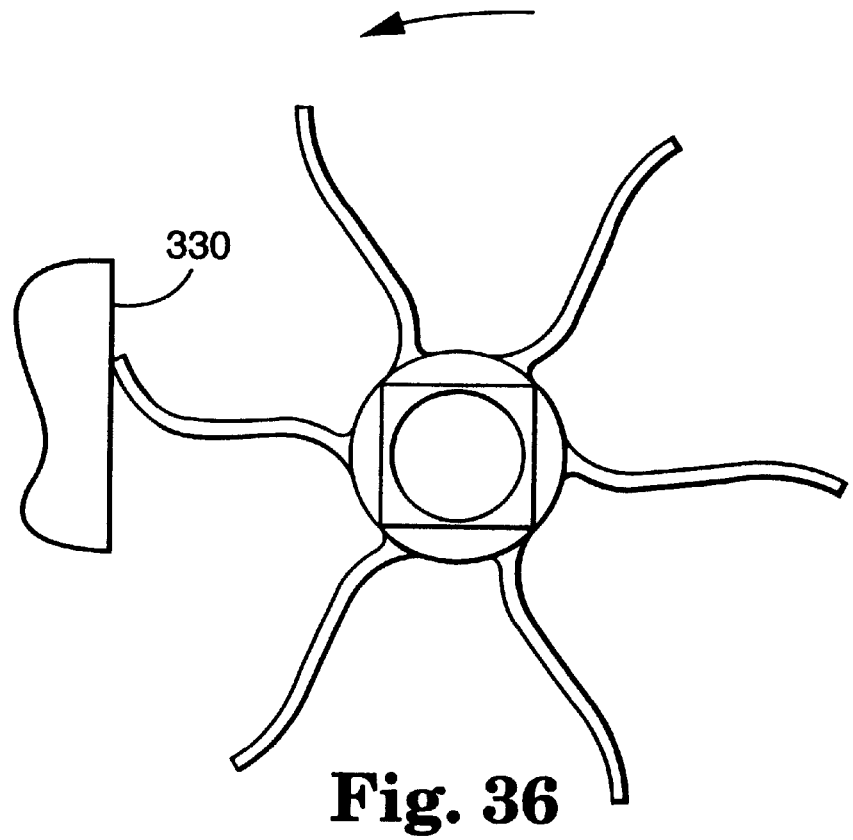
FIG. 36 is a side view of flexible blades and a hub for use in the dispenser shown in FIGS. 27–35.
Figure 37:
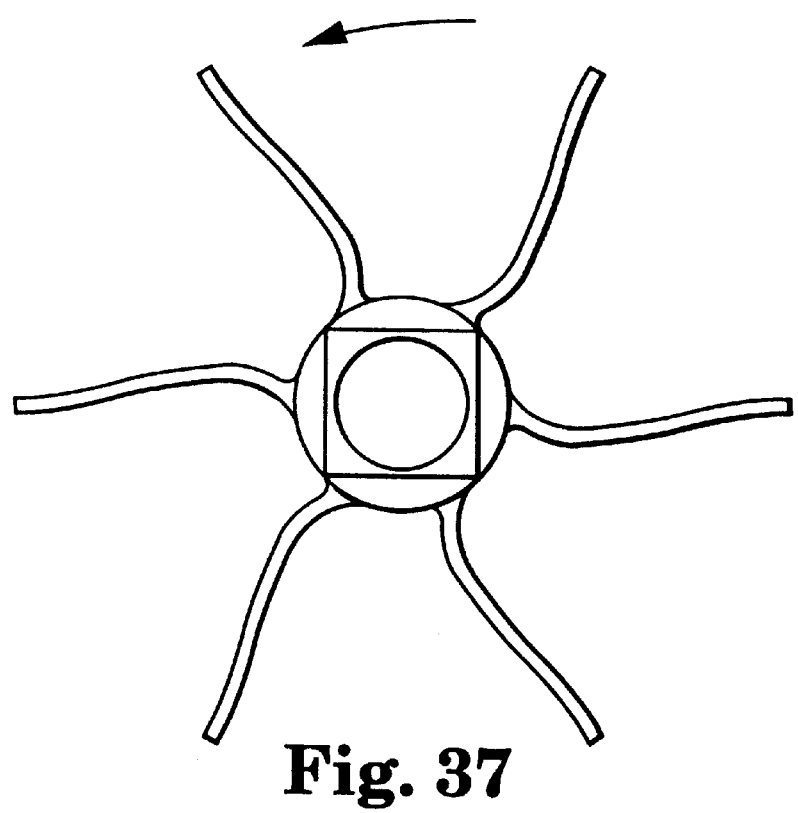
FIG. 37 is a side view of alternative flexible blades for use with the dispenser shown in FIGS. 27–35.

FIGS. 36 and 37 are side views illustrating examples of shapes of blades 336 for use in the cartridge of the dispenser 300. The arrows shown in the figures indicate the direction of during loading blades during loading of the dosage chamber 332. The general purpose finite element code ANSYS® was used to analyze the blades 336, dosage member 330, dosage chamber 332 and reservoir 311, and to generate the geometry of the blades shown in FIGS. 36 and 37. A static solution procedure was used to determine displacements, stresses, and strains occurring in the components under operating conditions. The time dependent effects of inertia and damping were assumed to be negligible, and frictionless contact was assumed. The governing equation for the static analysis was:

[K]{u}={F} where:

[K] is the global stiffness matrix

{u} is the vector of unknown displacements, and

{F} is the vector of applied loads.

The global stiffness matrix is the assemblage of the individual element stiffness matrices. These matrices are functions of the element geometry, type and material properties. Two-dimensional beam elements were used to represent the blades. A depth of 0.098 inches was assumed for the blades and the blade thickness was assumed to vary linearly between the blade base and tip. The dosage member 330 was assumed to be rigid member as well as the hub for the blades 336.

Parametric modeling procedures were used so that numerical design optimization techniques could be employed. An Ultem™ material and its characteristics (e.g. an elastic modulus of 420,000 psi, Poisson's ratio of 0.4 and a Yield Stress of 22,000 psi) were fed into the ANSYS® code, and a state space approach to optimization was utilized. The dependence of an objective function on various design variables (e.g. such as material characteristics) was defined. Based on a trial analysis, the objective function was expressed as an approximate polynomial function of the design variables. The objective function was defined to maximize the change in the angle between the blade tip and metering sleeve 330 as the blade 336 passes over the sleeve 330. The design variables used in the blade optimization included the thickness of the blade at the hub and at the tip, the slopes of the base and tip, and the angular offset between the base and tip. A single state variable constraint was defined which required the maximum stress in the blade to remain below the yield stress level of the blade material.

To account for the change in element stiffness as the blade deflects, ANSYS® used a Newton-Raphson method to update the stiffness matrix and force vector until convergence to equilibrium was achieved. The governing equation for finite element static analyses incorporating the Newton-Raphson procedure is $$[K_T]_{i-1}\{\Delta u\}_i = \{F^A\} - \{F^{NR}\}_{i-1}$$

where $[K_T]_{i-1}$ is the tangent stiffness matrix evaluated at iteration i−1, $\{\Delta u\}_i$ is the incremental displacement vector ($\{\Delta u\}_i = \{u\}_i - \{u\}_{i-1}$)

$\{F^A\}$ is the vector of applied loads, and $\{F^{NR}\}_{i-1}$ is the vector of Newton-Raphson restorative loads.

Several assumptions were made. For example, the ranges of the slope angles for the blade's base and tip were chosen to generate a reasonable blade geometry. The thickness of the blades varied linearly from preferably about 0.02 inches at the blade hub to about 0.01 inches at the tip. Preferably the thickness of the blades varies linearly from about 0.011 inches to about 0.014 inches, and the blade has a height of 0.098 inches. The blade 336 length along its spline shape may be approximately 0.273 inches.

The shapes of the blades shown in FIGS. 36 and 37 were provided by using the above described optimization techniques. The leading surfaces of the blades have both a concave and a convex portion. For the blades shown in FIG. 36, the values of all design variables could vary within their defined ranges, and an initial angle between the blade tip and dosing member was predicted to be 14 degrees. The contact force generated as the blade tip passed over the dosage chamber of the metering sleeve was 0.4 pounds. For the blades shown in FIG. 37, the slope of the blade at its base (at its intersection with the hub) was set to an upper limit of sixty (60) degrees, and an initial angle between the blade tip and metering sleeve was predicted to be 19 degrees. The contact force generated as the blade tip passed over the dosage chamber of the metering sleeve was 0.8 pounds.

The above identified program made several assumptions which may render the shapes of the blades shown in FIGS. 36 and 37 less desirable than other potential shapes for the blades. For example, two dimensional loading and response were assumed for elements and out of plane loading was not taken into account. Non-uniform loading of the blade's cross section may induce torsional stresses and deformation. Frictionless contact was assumed, and thus the effect of friction on torque and stress levels was not taken into account. Additionally, the assumptions of maximum stresses and linear elastic behavior may effect the analysis.

The cartridge includes dosage member 330. The dosage member 330 comprises a generally flat planar membrane or plate that is adapted to be releasably connected to a sleeve 389 of the base portion of the dispenser 300 by means such as hook shaped latch 331. The dosage member may be constructed from a metal such as brass or grade 304 stainless steel, or even a high strength plastic material. The dosage member 330 may have a thickness from about 0.047 inches to about 0.18 inches, and the chamber 332 may be sized according to the dose of the particular medicament to be delivered. The dosage member may be arranged relative to the blades 336 as shown in FIG. 36 or may instead be tilted from that orientation.

The cartridge also includes portions of a pressurization assembly including portions of a pressure reservoir 322 for intermittently storing a deagglomeration pressure, and a pressure outlet 323 for releasing the deagglomeration pressure from the pressure reservoir 322. The remaining portions of the pressurization assembly may be found in the base assembly including the remaining portion of the pressure reservoir 322 (FIG. 28) and a pressurization member 324 for reproducibly generating a deagglomeration pressure sufficient to deagglomerate the dose within the dosage chamber and expel the deagglomerated dose into medicament delivery passageway 316.

Like the dosage member 30, the dosage member 330 comprises a sealing surface for releasably sealing the pressure outlet 323 so that the pressure reservoir 322 may intermittently store the deagglomeration pressure. Also, when the cartridge and base are assembled, a sealing means is present between the cartridge portion of the pressure reservoir 322 and the base portion of the pressure reservoir.

The piston 324 is movable between retracted (FIGS. 28, solid lines) and extended positions (FIG. 28, dashed lines)

such that (1) movement of the piston 324 from the extended toward the retracted position draws ambient air into the pressure reservoir 322, and (2) movement of the piston 324 from the retracted toward the extended position pressurizes air within the pressure reservoir 322 to the deagglomeration pressure when the sealing surface of the dosage member 330 seals the pressure outlet 323. For example, the piston 324 may have a maximum outer diameter of about 0.5 inches, and the pressure chamber may provide a pressure of about 50 pounds per square inch.

When the pressure outlet 323 is covered by sealing surfaces of the dosage member 330, the piston 324 utilizes a one-way valve means which affords flow of air into the pressure chamber 322 while the piston 324 retracts. The one-way valve also prevents the flow of air out of the pressure chamber 322 when the piston 324 is moved from the retracted to the extended position. Such a means may comprise a slit in an elastomeric portion 319 of the piston 324.

Like the dosage chamber 30, the dosage chamber 330 is movable relative to a pressure outlet 323 between a load position (FIG. 34) with the dosage chamber 332 in communication with the medicament reservoir 311, and with a sealing surface of the dosage member 330 sealingly covering pressure outlet 323, and a registered position (FIGS. 30, 33 and 35) with the dosage chamber 332 in communication with the pressure reservoir 322 through the pressure outlet 323.

The dispenser 300 also includes an actuator for registering the pressure outlet 323 and the dosage chamber 332 in a registered position (FIGS. 31 and 33) so that the deagglomeration pressure forcibly expels the predetermined, agglomerated dose from the dosage chamber 332 in deagglomerated form suitable for inhalation therapy and into optional medicament delivery passageway 316. The medicament expelled from the chamber 332 passes through medicament delivery passageway 316 and into a user's inhalation airstream within an inhalation airway passageway 379.

The inhalation airway passageway 379 affords passage of a user inspiratory airflow. To generate airflow through the passageway 379, the a user places his or her mouth on the mouthpiece portion 315 and inhales. Preferably, the inhalation airway passageway 379 is formed by at least one hole 329 (FIG. 27) in the housing 314. The passageway 379 is in fluid communication with the medicament delivery passageway 316.

The actuator comprises a biasing means such as spring 388 for biasing the dosage chamber 332 toward the registered position, and releasable retaining means for releasably retaining the dosage chamber 332 in a load position (FIGS. 34, 35) against the bias of spring 388.

The releasable retaining means of the dispenser 300 comprises an inhalation activated assembly 380 that is in fluid communication with and preferably mounted within the inhalation airway passageway 379. A user's inhalation airstream communicates with a cavity in the housing in which the inhalation activated assembly 380 is mounted.

The inhalation activated assembly 380 releases the dosage chamber 332 in response to user inspiratory airflow through the inhalation airway passageway 379 to afford movement of the dosage chamber 332 to the registered position under the bias of spring 388.

FIGS. 31–35 illustrate the location of the inhalation activated assembly 380 relative to the medicament delivery passageway 316. While the inhalation airway passageway 379 is in fluid communication with the medicament delivery passageway 316, the inhalation activated assembly 380 is preferably not directly in the path of the medicament delivery passageway 316 so that dry powder medicament will not impinge on the assembly 380.

The inhalation activated assembly 380 comprises a base portion 381 having a first receiving surface 382. The base portion 381 is fixed relative to the housing 314 and is preferably integrally molded on interior surfaces of the housing 314. The receiving surface 382 preferably comprises a ledge portion at the end of a channel that is integrally formed on the interior surfaces of the housing 314.

Figure 33:
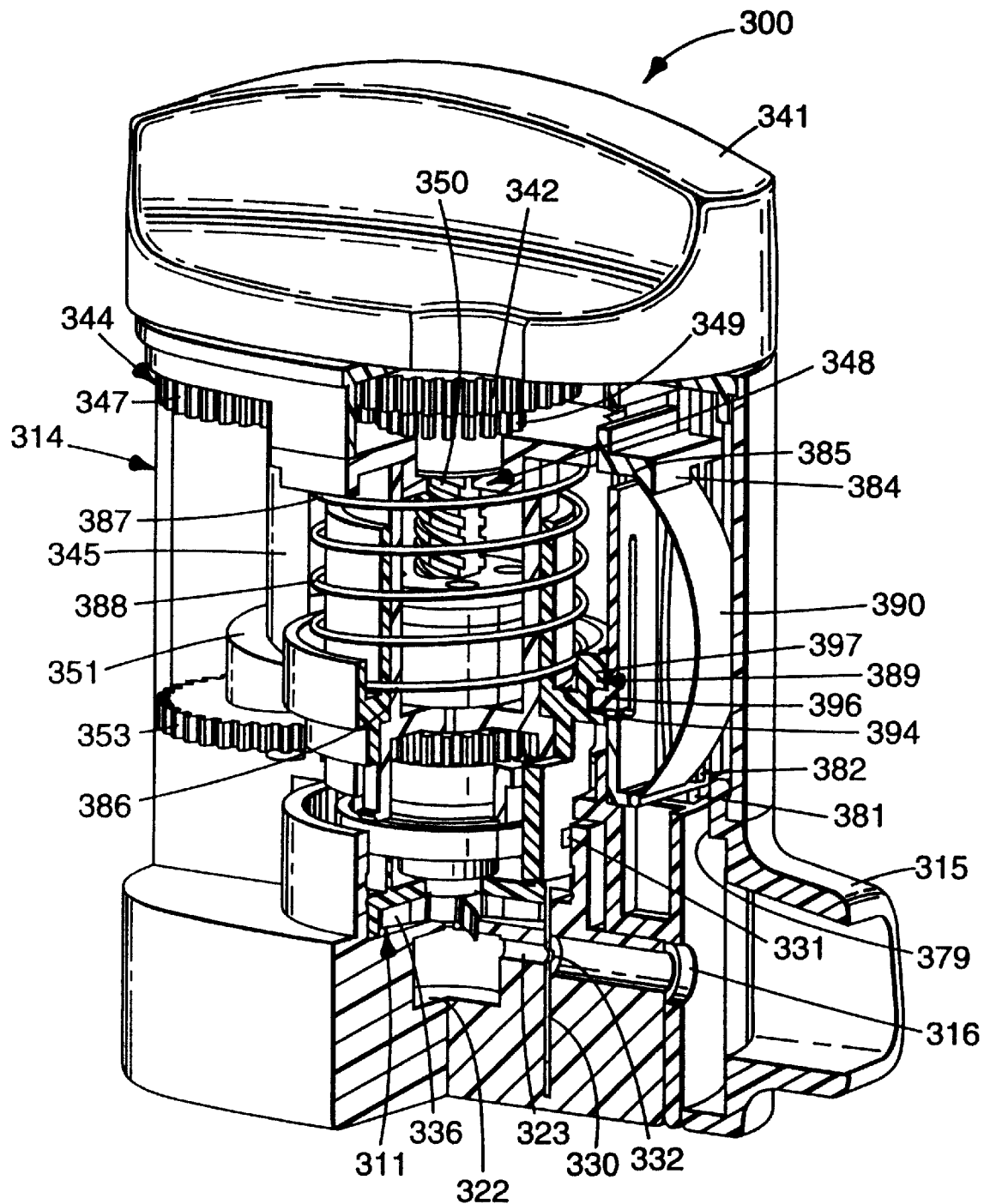
Figure 34:
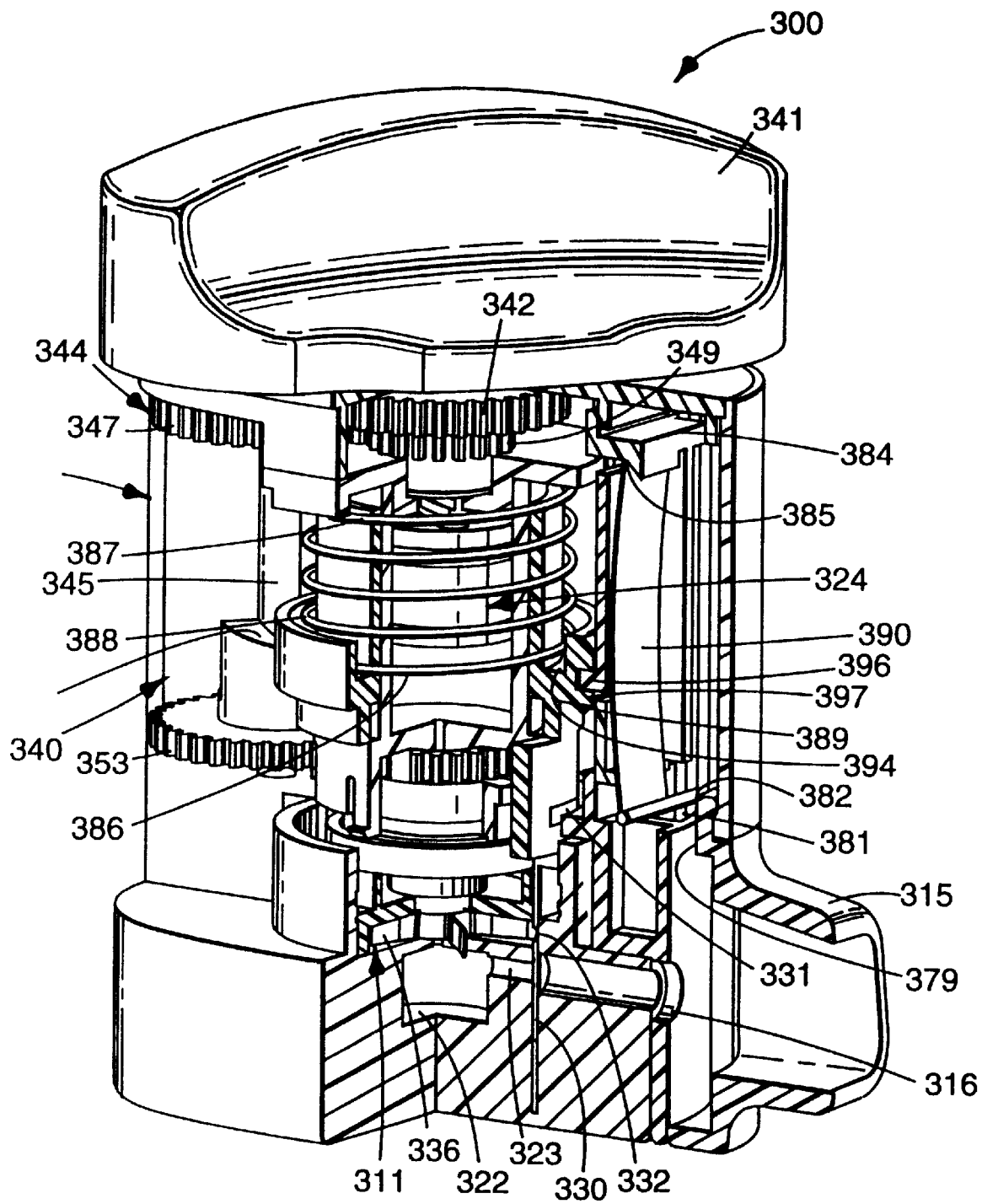
Figure 35:
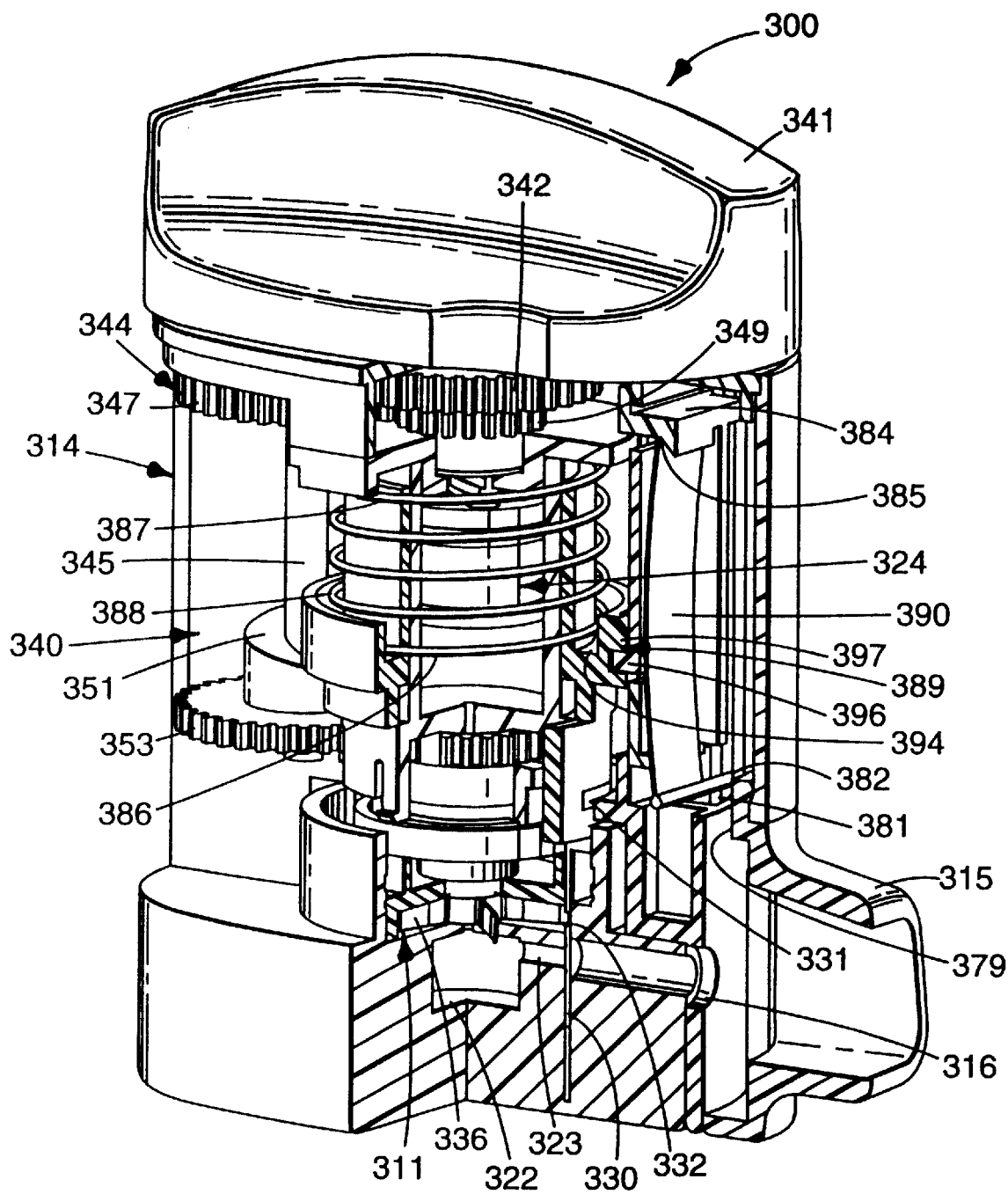

The inhalation activated assembly 380 also comprises an actuating body or slider 384 having a second receiving surface 385. As seen in FIGS. 33 through 35, the slider 384 is mounted for movement relative to the base portion between armed (FIGS. 34 and 35) and fired (FIG. 33) positions.

The spring 388 biases the slider 384 toward the fired position. The spring 388 has a pair of ends 387 and 386. The force of the spring 388 is transmitted to the slider 384 via sleeve 389. The slider 384 is connected to the generally cylindrical sleeve 389 which is mounted generally coaxial about the pressure reservoir 322. The slider 384 may comprise a flange 396 that may be snap fit between ribs 397 on the sleeve 389. The sleeve 389 is movable relative to the reservoir 322.

The sleeve 389 has shoulder surfaces 394. The first end 387 of the spring 388 abuts a portion of the housing 314. For example, that portion of the housing may be supplied by a plate 395 (FIG. 27) that is connected to the rest of the interior surfaces of the dispenser housing 314 by a fastening means such as a snap fit. The second end 386 of the spring 388 abuts the sleeve shoulder surfaces 394.

The inhalation activated assembly also includes an over center toggle joint linkage comprising a flexible, resilient membrane 390 having a first end abutting the first receiving surface 382 and a second end abutting the second receiving surface 385, and first and second major surfaces.

The flexible membrane 390 is movable between (1) a first position (FIGS. 28, 34 and 35) where it releasably retains the slider 384 in the armed position (and thus the dosage chamber 332 in the load position) against the bias of spring 388, and (2) a second position (FIGS. 31 through 33) which is over center relative to the first position. When the flexible membrane 390 moves from the first toward the second position, it affords movement of the slider 384 from the armed to the fired position under the bias of spring 388. The flexible membrane 390 is mounted in the housing 314 such that, during inspiration through the inhalation airway passageway 379, the membrane 390 is biased from its first position toward its second position.

The slider 384 has surfaces which abut a major side surface of the membrane 390 in the first position to assist in retaining the slider in the position shown in FIGS. 28, 34 and 35 against the bias of spring 388. Preferably the surfaces of the slider 384 approximate the shape of the major surface of the membrane 390.

The flexible membrane 390 may be constructed from stainless steel having a modulus of elasticity of at least 28×10 EXP 6 psi, and a Yield strength of at least 165×10 EXP 3 psi. The flexible membrane 390 has an arc length of approximately 1.25 inches, a width of about 0.5 inches, and a thickness of about 0.0025 inches. In the first position, the flexible membrane 390 is generally arcuate and has a radius of curvature of approximately 19.53 inches, and in the second position, the flexible membrane 390 is also arcuate and has a radius of curvature of approximately 0.811 inches. Between the first and second positions, a major surface of the membrane 390 changes from a convex to a concave shape. Preferably, the flexible membrane is constructed from a resilient material with "memory". The material should return the membrane from the second position to the first position when the load on the membrane due to the spring 388 is removed.

According to another aspect of the present invention, the dispenser 300 includes a handle 341 movable relative to the housing 314, and a transmission 340 for transmitting the movement of the handle 341 to the piston 324, dosage chamber 332 and blades 336.

The handle 341 is movable relative to the housing 314 between first (FIGS. 33 and 35) and second (FIG. 34) positions. Preferably the motion of the handle 341 between the first and second positions is generally pivotal with the angle between the first and second positions less than about 130 degrees.

Movement of the handle 341 from the first toward the second position: (1) moves the piston 324 from the extended to the retracted position, and (2) moves the dosage member 330 from the registered to the load position against the bias of the spring 388 and so that the sealing surface of the dosage member 330 seals the pressure outlet 323. Movement of the handle 341 from the second toward the first position (1) moves the piston 324 from the retracted to the extended position to pressurize the pressure reservoir 322 to the deagglomeration pressure, and (2) causes the blades 336 to transfer the powder from the medicament reservoir 311 to the dosage chamber 332. At this point the dispenser 300 is ready to be actuated by assembly 380 which is triggered by a user's inhalation through inhalation passageway 379.

FIGS. 33 through 35 sequentially illustrate the operation of the transmission wherein FIG. 33 illustrates the dispenser 300 after it has been fired, and FIG. 35 illustrates the dispenser which is ready to be actuated by the assembly 380.

The arrows shown in FIG. 27 illustrate the direction of motion of the various elements of the transmission when the handle 341 is moved from the first to the second position. During movement of the handle 341 from the first to the second position, the transmission 340 (1) moves the piston 324 from the extended position toward the retracted position, and (2) moves the chamber 332 from the registered position to the load position by moving the slider 384 from the fired to the armed position against the bias of spring 388 so that the flexible membrane 390 may move from the second to the first position to retain the slider 384 in the armed position. Once the handle has been moved from the first to the second position, the spring 388 bias on the flexible member 390 (which causes the flexible member to assume the shape shown in FIG. 33) is removed and the flexible member's own inherent resiliency causes it to assume the shape shown in FIG. 34.

The direction opposite the arrows shown in FIG. 27 is the direction of motion of the various elements of the transmission when the handle 341 is moved from the second to the first position. Reversing the direction of movement of the handle 341 to move it from the second toward the first position: (1) moves the piston 324 from the retracted position toward the extended position to pressurize the pressure reservoir 322, and (2) moves the blades 336 to transfer the dry powder medicament from the reservoir 311 to the chamber 332. Once the handle has been moved from the second to the first position, the flexible membrane 390 releasably retains the slider 384 in the armed position (and thus the dosage chamber 332 in the load position) against the bias of spring 388.

The transmission comprises a first drive gear 342 (e.g. a gear having a pitch of approximately 0.75 inches, 36 teeth, 48 pitch) having a first shaft 343 connected to the handle 341. The first drive gear 342 is rotatable in (1) a first direction (the direction of the arrow in FIG. 27) when the handle 341 is moved from the first to the second position, and (2) a second direction, generally opposite the first direction, when the handle 341 is moved from the second to the first position.

The transmission also comprises a spur gear assembly 344 comprising a second shaft 345 axially spaced from the first shaft 343, a pinion gear 346 (e.g. a gear having a pitch of about 0.417 inches, 20 teeth), and a second drive gear 347 (e.g. a gear having a pitch of about 0.750 inches, 36 teeth) connected to the pinion 346 gear so that it rotates in the same direction as the pinion gear 346. The spur gear assembly 344 is mounted such that the pinion gear 346 meshes with the first drive gear 342 so that it rotates in the opposite direction of the first drive gear 342.

The transmission also includes a lead screw assembly 348 operatively associated with the second drive gear 347 for moving the piston 324 from the extended position toward the retracted position during the movement of the handle 341 from the first to the second position. The lead screw assembly 348 also moves the piston 324 from the retracted position toward the extended position to pressurize the pressure reservoir 322 during the movement of the handle 341 from the second to the first position.

Preferably the lead screw assembly 348 comprises a drive nut 349 (e.g. having a pitch of about 0.417, 20 teeth, and an internal diameter of about 0.18 inches) having external gear teeth for engaging or meshing with the second drive gear 347 such that the drive nut 349 rotates in a direction generally opposite the direction of rotation of the second drive gear 347, and internal threaded surfaces. The piston 324 has a lead screw portion having external threads 350 for engaging the internal threads of the drive nut 349. Opposite rotation of the drive nut 349 causes the piston 324 to reciprocate between the extended and retracted positions.

The transmission also comprises a one-way cam assembly operatively associated with the second shaft 345. The one-way cam assembly moves the dosage chamber 332 from the delivery position to the load position, and moves the slider 384 from the fired to the armed position during the movement of the handle 341 from the first to the second position. The one-way cam assembly is connected to the second shaft 345 and includes helical cam surfaces 351 for engaging bearing surfaces 352 on the sleeve 389. The cam surfaces 351 move the slider 384 (via its link with the sleeve 389) from the fired to the armed position during the movement of the handle 341 from the first to the second position. In this manner the bias on the membrane 390 provided by the spring 388 may be removed to allow the membrane 390 to return to the shape shown in FIG. 34 by means of its own inherent resiliency.

The transmission also comprises a one-way drive assembly for moving the blades 336 such that dry powder medicament is transferred from the reservoir 311 to the dosage chamber 323 during movement of the handle 341 from the second to the first position. Preferably the one-way drive assembly comprises a one-way clutch 358 (FIG. 30) for driving the blades 336 in a predetermined powder loading direction (note the arrows in FIGS. 36 and 37).

The one-way drive assembly comprises a third drive gear 353 (e.g. a gear having a maximum pitch of about 0.750, 36 teeth) connected to the second shaft 345, and a clutch assembly comprising a driven gear 354 (e.g. a gear having a maximum pitch of about 0.417, 20 teeth) having teeth for engaging the third drive gear 353 so that the driven gear 354 rotates in a direction opposite the direction of rotation of the drive gear 353, and leaf spring gear clutch 355 (FIG. 27) attached to the driven gear 354 for rotation in the same direction as the direction of rotation of the driven gear 354.

The leaf spring gear clutch 356 engages the one-way gear clutch 358 to drive the blades 336 in the powder loading direction, and releases from the one-way gear clutch 358 when the leaf spring gear clutch 355 is rotated in a direction opposite the powder loading direction.

Portions of the transmission assembly are releasably coupled to the base assembly by the leaf spring gear clutch 355 and one way clutch 358. The dosage member 330 is releasably connected to the actuation sleeve 389 by the above described hook shaped latch 331. As noted above, sealing means are present between the base assembly portion of the reservoir 322 and the cartridge assembly portion of the reservoir 322.

Operation

Operation of the dispenser 300 will now be described with reference to FIGS. 27 through 35 with emphasis on FIGS. 33 through 35.

FIG. 33 illustrates the position of the elements of the transmission and actuator of the dispenser 300 prior to use and during the majority of the time of the life of the dispenser. In this position, the pressure reservoir 322 is not pressurized and the dosage chamber 332 is not loaded.

The transmission 340 and inhalation activated assembly 380 provide a device which is easy and convenient to use. To use the dispenser, a user simply moves the handle 341 from the first toward the second position and then reverses the direction of movement of the handle 341 to move it from the second to the first position. An optional leaf spring rib shown in FIG. 27 near inhalation activated assembly 380 may be used to indicate the position of the handle 341 relative to housing 314.

Movement of the handle 341 causes the above described effects and causes the elements to assume the orientations generally shown in FIG. 35. In this position, the dispenser is ready for a user to inhale through mouthpiece 315. However, the user need not rush to fire the device as a user need not coordinate movement of the handle 341 with inhalation.

When a user inhales through passageway 379, the membrane 390 is biased over center toward the position shown in FIG. 34. Once the member 390 initially moves over center, the bias of spring 388 causes the member to rapidly assume the shape shown in FIG. 33 and also actuates the dispenser 300 in the manner described above.

The transmission 340 and assembly 380 require minimal coordination by a user between arming and actuation of the dispenser 300. The dispenser 300 does not require a complicated sequence of events as a user simple moves the handle and inhales. This feature is believed to be particularly desirable when a user is suffering from an ailment which may distract the user from proper operation of the device.

The present invention has now been described with reference to several embodiments thereof. It will be apparent to those skilled in the art that many changes can be made in the embodiment described without departing from the scope of the present invention. For example, in each of the species the dosage chamber and medicament delivery passageway remain at generally ambient pressure and the pressure reservoir is pressurized to the deagglomeration pressure. Alternatively, both the dosage chamber and the pressure reservoir may be pressurized to the deagglomeration pressure and the pressure differential may be provided by retaining the medicament delivery passageway at ambient pressure. Thus the scope of the present invention should not be limited to the structure described in this application, but only by structures described by the language of the claims and the equivalents of those structures.

What is claimed is:

1. A device for reproducibly dispensing multiple, individual doses of a micronized, dry powder medicament comprising:

a housing, a medicament reservoir for holding a bulk supply of dry powder medicament, a dosage member having a dosage chamber for releasably containing a predetermined, agglomerated dose of said dry powder medicament, an agglomerator for transferring a quantity of the dry powder medicament from said medicament reservoir to said dosage chamber and for packing said quantity into said predetermined, agglomerated dose within said dosage chamber, a pressurization assembly including:

a pressurization member for reproducibly generating a deagglomeration pressure sufficient to deagglomerate the dose within said dosage chamber, a pressure reservoir for intermittently storing said deagglomeration pressure, and a pressure outlet for releasing said deagglomeration pressure from said pressure reservoir; and an actuator for registering said pressure outlet and said dosage chamber in a registered position so that said deagglomeration pressure forcibly expels the predetermined, agglomerated dose from the dosage chamber in deagglomerated form suitable for inhalation therapy.

2. A device according to claim 1 wherein said dosage member comprises a sealing surface for sealing said pressure outlet so that said pressure reservoir may store said deagglomeration pressure.

3. A device according to claim 2 wherein said pressurization member is movable between retracted and extended positions such that (1) movement of said pressurization member from said extended toward said retracted position draws ambient air into said pressure reservoir, and (2) movement of said pressurization member from said retracted toward said extended position pressurizes air within said pressure reservoir when said sealing surface seals said pressure outlet, said dosage chamber is movable relative to said pressure outlet between a load position with said dosage chamber in communication with said medicament reservoir and said registered position with the dosage chamber in communication with the pressure reservoir through said pressure outlet, and said agglomerator is movable relative to said medicament reservoir to pack the powder into the dosage chamber when said dosage chamber is in the load position.

4. A device according to claim 1 wherein when said actuator registers said pressure outlet and said dosage chamber in said registered position, said dosage chamber is situated generally immediately adjacent said pressure outlet.

5. A device according to claim 1 further including a medicament delivery passageway affording passage of the dose that has been expelled from the dosage chamber in deagglomerated form suitable for inhalation therapy, wherein said medicament delivery passageway is substantially free of structure for deagglomerating the powder beyond the deagglomeration provided by the pressurization assembly.

6. A device for reproducibly dispensing multiple, individual doses of a micronized, dry powder medicament comprising:

a housing, a medicament reservoir for holding a bulk supply of dry powder medicament, a dosage member having a dosage chamber for releasably containing a predetermined, agglomerated dose of said dry powder medicament, an agglomerator for transferring a quantity of the dry powder medicament from said medicament reservoir to said dosage chamber and for packing said quantity into said predetermined, agglomerated dose within said dosage chamber, a pressurization assembly including:

a pressurization member for reproducibly generating a deagglomeration pressure sufficient to deagglomerate the dose within said dosage chamber, a pressure reservoir for intermittently storing said deagglomeration pressure, and a pressure outlet for releasing said deagglomeration pressure from said pressure reservoir;

an actuator for registering said pressure outlet and said dosage chamber in a registered position so that said deagglomeration pressure forcibly expels the predetermined, agglomerated dose from the dosage chamber in deagglomerated form suitable for inhalation therapy, said dosage member comprising a sealing surface for sealing said pressure outlet so that said pressure reservoir may store said deagglomeration pressure, said pressurization member being movable between retracted and extended positions such that (1) movement of said pressurization member from said extended toward said retracted position draws ambient air into said pressure reservoir, and (2) movement of said pressurization member from said retracted toward said extended position pressurizes air within said pressure reservoir when said sealing surface seals said pressure outlet, said dosage chamber is movable relative to said pressure outlet between a load position with said dosage chamber in communication with said medicament reservoir and said registered position with the dosage chamber in communication with the pressure reservoir through said pressure outlet, said agglomerator being movable relative to said medicament reservoir to pack the powder into the dosage chamber when said dosage chamber is in the load position, a handle movable relative to said housing, and a transmission for transmitting the movement of the handle to the pressurization member, dosage chamber and agglomerator.

7. A device according to claim 6 wherein said actuator comprises a biasing means for biasing said dosage chamber toward said registered position.

8. A device according to claim 7 wherein said handle is movable relative to said housing between first and second positions wherein:

movement of said handle from said first toward said second position is adapted to (1) move said pressurization member from said extended to said retracted position, and (2) move said dosage member from said registered to said load position against the bias of said biasing means and so that said sealing surface seals said pressure outlet, and movement of said handle from said second toward said first position is adapted to (1) move said pressurization member from said retracted to said extended position to pressurize said pressure reservoir to said deagglomeration pressure, and (2) cause said agglomerator to transfer the powder from the medicament reservoir to the dosage chamber; and wherein said actuator includes a releasable retaining means for releasably retaining said dosage chamber spaced from said registered position against the bias of said biasing means.

9. A device according to claim 8 wherein said housing includes an inhalation airway passageway affording passage of a user inspiratory airflow, and said releasable retaining means comprises an inhalation activated assembly in communication with said inhalation airway passageway, wherein said inhalation activated assembly releases said dosage chamber in response to user inspiratory airflow to afford movement of said dosage chamber to said registered position under the bias of said biasing means.

10. A device for reproducibly dispensing multiple, individual doses of a micronized, dry powder medicament comprising:

a housing a medicament reservoir for holding a bulk supply of dry powder medicament, a dosage member having a dosage chamber for releasably containing a predetermined, agglomerated dose of said dry powder medicament, an agglomerator for transferring a quantity of the dry powder medicament from said medicament reservoir to said dosage chamber and for packing said quantity into said predetermined, agglomerated dose within said dosage chamber, a pressurization assembly including:

a pressurization member for reproducibly generating a deagglomeration pressure sufficient to deagglomerate the dose within said dosage chamber, a pressure reservoir for intermittently storing said deagglomeration pressure, and a pressure outlet for releasing said deagglomeration pressure from said pressure reservoir, and an actuator for registering said pressure outlet and said dosage chamber in a registered position so that said deagglomeration pressure forcibly expels the predetermined, agglomerated dose from the dosage chamber in deagglomerated form suitable for inhalation therapy, wherein said actuator registers said pressure outlet with said dosage chamber by moving progressively increasing portions of said pressure outlet and said dosage chamber into alignment so that said deagglomeration pressure is directly exposed to progressively increasing portions of said dosage chamber through said pressure outlet.

11. A device according to claim 10 wherein said actuator comprises a biasing means for biasing said dosage chamber toward said registered position, and releasable retaining means for releasably retaining said dosage chamber spaced from said registered position against the bias of said biasing means.

12. A device according to claim 11 wherein said housing includes an inhalation airway passageway affording passage of a user inspiratory airflow, and said releasable retaining means comprises an inhalation activated assembly in communication with said inhalation airway passageway, wherein said inhalation activated assembly releases said dosage chamber in response to said user inspiratory airflow to afford movement of said dosage chamber to said registered position under the bias of said biasing means.

13. A device according to claim 10 wherein the dosage chamber defines a loading axis which is generally normal to the surfaces of the dosage member defining an end of the dosage chamber, and the agglomerator is mounted to move relative to said dosage chamber and across said dosage chamber to provide a positive packing force that has a component which is generally parallel to said loading axis, wherein the packing force increases as said agglomerator moves across at least a portion of said dosage chamber.

14. A device according to claim 13 wherein said agglomerator comprises a flexible, resilient blade, and said flexible blade progressively, increasingly bends to increase the component of said packing force which is generally parallel to said loading axis as the blade moves across at least a portion of said dosage chamber.

15. A device according to claim 10 wherein said agglomerator engages dry powder medicament within said medicament reservoir to transfer the medicament from said medicament reservoir to said dosage chamber and to pack the medicament into said predetermined dose.

16. A device for reproducibly dispensing multiple, individual doses of a micronized, dry powder medicament comprising:

a housing defining a device orientation, means for providing an agglomerated, predetermined dose of powdered medicament within a dosage chamber of a dosage member generally independent of the orientation of the device, a pressurization assembly including:
a pressurization member for reproducibly providing a deagglomeration pressure,
a pressure reservoir for intermittently storing said deagglomeration pressure, and
a pressure outlet for releasing said deagglomeration pressure from said pressure reservoir; and an actuator for registering said pressure outlet and said dosage chamber in a registered position so that said deagglomeration pressure forcibly expels the predetermined dose from the dosage chamber in deagglomerated form suitable for inhalation therapy.

17. A device according to claim 16 wherein the dosage chamber defines a loading axis which is generally normal to surfaces of the dosage member which define an end of the dosage chamber, and said means for providing an agglomerated dose comprises:
a medicament reservoir for holding a bulk supply of dry powder medicament, and
an agglomerator mounted to move relative to said dosage chamber and across said dosage chamber to provide a positive powder packing force that has a component which is generally parallel to said loading axis to transfer dry powder medicament from said medicament reservoir to said dosage chamber and to pack the dry powder medicament into said agglomerated, predetermined dose in the dosage chamber, wherein the packing force increases as said agglomerator moves across at least a portion of said dosage chamber.

18. A device according to claim 17 wherein said agglomerator comprises a flexible blade, and said flexible blade progressively, increasingly bends to increase the component of said packing force which is generally parallel to said loading axis as the blade moves across at least a portion of said dosage chamber.

19. A device according to claim 16 further including a medicament delivery passageway affording passage of the dose that has been expelled from the dosage chamber in deagglomerated form to a user's respiratory system, wherein said medicament delivery passageway is substantially free of structure for deagglomerating the powder beyond the deagglomeration provided by the pressurization assembly.

20. A device for reproducibly dispensing multiple, individual doses of a micronized, dry powder medicament comprising:

a housing, means for providing an agglomerated, predetermined dose of powdered medicament within a dosage chamber of a dosage member, a pressurization assembly including:
a pressurization member for reproducibly generating a deagglomeration pressure sufficient to deagglomerate the dose within said dosage chamber,
a pressure reservoir for intermittently storing said deagglomeration pressure, and
a pressure outlet for releasing said deagglomeration pressure from said pressure reservoir; and an actuator for registering said pressure outlet and said dosage chamber in a registered position so that said deagglomeration pressure forcibly expels the predetermined, agglomerated dose from the dosage chamber in deagglomerated form suitable for inhalation therapy; said actuator registering said pressure outlet with said dosage chamber by moving progressively increasing portions of said pressure outlet and said dosage chamber into alignment so that said deagglomeration pressure is exposed to progressively increasing portions of said dosage chamber through said pressure outlet.

21. A device according to claim 20 further including a medicament delivery passageway affording passage of the dose that has been expelled from the dosage chamber in deagglomerated form to a user's respiratory system, wherein said medicament delivery passageway is substantially free of structure for deagglomerating the powder beyond the deagglomeration provided by the pressurization assembly.

22. A device according to claim 20 wherein the dosage chamber defines a loading axis which is generally normal to surfaces of the dosage member which define an end of the dosage chamber, and said means for providing an agglomerated dose comprises:
a medicament reservoir for holding a bulk supply of dry powder medicament, and
an agglomerator mounted to move relative to said dosage chamber and across said dosage chamber to provide a positive powder packing force that has a component which is generally parallel to said loading axis to transfer dry powder medicament from said medicament reservoir to said dosage chamber and to pack the dry powder medicament into said agglomerated, predetermined dose in the dosage chamber, wherein the packing force increases as said agglomerator moves across at least a portion of said dosage chamber.

23. A device according to claim 22 wherein said agglomerator comprises a flexible, resilient blade, and said blade progressively, increasingly bends to increase the component of said packing force which is generally parallel to said loading axis as the blade moves across at least a portion of said dosage chamber.

24. A medicament dispenser having a transmission, said dispenser comprising a housing,
a handle movable relative to said housing,
a medicament reservoir for storing a bulk supply of medicament,
a pressurization assembly comprising a pressure reservoir having a pressure outlet, and a pressurization member movable between retracted and extended positions;
a dosage member having a dosage chamber movable relative to said pressure outlet from a registered position with the dosage chamber in communication with the pressure reservoir through said pressure outlet and a load position spaced from said registered position and opening into said medicament reservoir, and
transfer means for transferring medicament from said reservoir to said dosage chamber,
wherein said transmission comprises:
means for transmitting the movement of the handle to the pressurization member, dosage member and transfer means.

25. A medicament dispenser according to claim 24 wherein the medicament dispenser has a sealing surface means for intermittently sealing the pressure outlet,
wherein movement of said pressurization member from said extended toward said retracted position draws ambient air into the pressure reservoir, and movement of said pressurization member from said retracted toward said extended position pressurizes air within said pressure reservoir when the pressure outlet is sealed, and
said handle is movable relative to said housing between first and second positions wherein:
movement of said handle from said first toward said second position is adapted to (1) move said pressurization member from said extended to said retracted position, (2) move said dosage member from said registered to said load position and (3) seal said pressure outlet with said sealing surface, and
movement of said handle from said second toward said first position is adapted to (1) move said pressurization member from said retracted to said extended position to pressurize said pressure reservoir, and (2) cause said transfer means to transfer the powder from the medicament reservoir to the dosage chamber.

26. A dispenser according to claim 24 wherein said dispenser has an inhalation activated assembly movable between prefired and fired positions, and
said transmission has a means for transmitting the movement of the handle to the inhalation activated assembly.

27. A dispenser according to claim 24 wherein said handle is pivotably movable between first and second positions, said transmission comprising:
a first drive gear having a first shaft connected to said handle, said first drive gear being rotatable in: (a) a first direction when said handle is moved from said first to said second position, and (b) a second direction, generally opposite said first direction, when said handle is moved from said second to said first position.

28. A dispenser according to claim 27 comprising:
a spur gear assembly comprising a second shaft spaced from said first shaft, a pinion gear and a second drive gear connected to the pinion gear so that it rotates in the same direction as the pinion gear, said spur gear assembly being mounted such that said pinion gear meshes with said first drive gear so that it rotates in the opposite direction of the first drive gear.

29. A dispenser according to claim 28 comprising: a lead screw assembly operatively connected to said second drive gear for moving the pressurization member from the extended position toward the retracted position during the movement of the handle from the first to the second position, and for moving the pressurization member from the retracted position toward the extended position to pressurize the pressure reservoir during the movement of the handle from the second to the first position,
a one-way cam assembly operatively associated with said second shaft, said one-way cam assembly being adapted to move the dosage member and dosage chamber from the registered position to the pre-registered position, and
a one-way drive assembly for moving the transfer means such that medicament is transferred from the medicament reservoir to the dosage chamber during movement of the handle from the second to the first position.

30. A transmission according to claim 29 wherein said lead screw assembly comprises a drive nut having external gear teeth for engaging said second drive gear such that the drive nut rotates in a direction generally opposite said second drive gear, and internal threaded surfaces,
said pressurization member having a lead screw having external threads for engaging said internal threaded surfaces,
wherein said pressurization member reciprocates between said extended and retracted positions.

31. A dispenser according to claim 30 wherein said one-way cam assembly is connected to said second shaft and includes helical cam surfaces for engaging bearing surfaces for an actuating body of an inhalation activated assembly,
wherein the cam surfaces move the actuating body from a fired to an armed position during the movement of the handle from the first to the second position.

32. A dispenser according to claim 24 wherein the transmission comprises:
control means operatively associated with said handle for (a) moving the pressurization member from the extended position toward the retracted position, (b) moving the dosage member and dosage chamber from the registered to the pre-registered position, and (c) moving an actuating body from a fired to an armed position against the bias of a biasing means such that an inherently resilient flexible membrane may move from a second to a first position to retain the actuating body in the armed position, during a portion of movement of the handle, and for (1) moving the pressurization member from the retracted position toward the extended position to pressurize the pressure chamber, and (2) moving the transfer means to transfer the medicament from the medicament reservoir to the dosage chamber, during another portion of movement of the handle.

33. A method of dispensing multiple individual doses of a dry powder medicament comprising the steps of:
   packing micronized particles of the medicament within a dosage chamber into a predetermined, agglomerated dose,
   generating a deagglomeration fluid pressure sufficient to deagglomerate the dose within the dosage chamber,
   intermittently storing the deagglomeration fluid pressure in a pressure reservoir having a pressure outlet for releasing the deagglomeration fluid pressure,
   sealing the pressure outlet; and
   then forcibly expelling the dose from the dosage chamber with the deagglomeration pressure in a deagglomerated form suitable for inhalation therapy by registering the pressure outlet and the dosage chamber when the pressure reservoir stores the deagglomeration fluid pressure to thereby release the sealed pressure outlet.

34. A method according to claim 33 further including the step of:
   flowing the deagglomerated dose to the respiratory system of a user through a medicament delivery passageway which is free of structure for substantial further deagglomeration of the medicament.

35. A dry powder medicament dispenser comprising:
   a housing including a mouthpiece portion adapted to be received in a user's mouth, said housing having:
   a medicament reservoir adapted for storing dry powder medicament,
   a medicament delivery passageway opening through said mouthpiece portion,
   a gas pressure chamber including a pressure outlet passageway generally adjacent said medicament delivery passageway,
   means for pressurizing gas within the gas pressure chamber above ambient pressure,
   a dosage member comprising a sealing surface and having a dosage chamber, and
   means mounting said dosage member for movement between (1) a load position with the dosage chamber opening into the medicament reservoir and with the sealing surface of the dosage member sealing pressure within the gas pressure chamber, to (2) a delivery position with the dosage chamber extending between the pressure outlet passageway and the medicament delivery passageway.

36. A dispenser according to claim 35 wherein progressively increasing portions of the pressure outlet passageway, the dosage chamber, and the medicament delivery passageway become aligned during movement of the dosage member from the load position to the delivery position to afford dispersion of the dry powder medicament.

37. A dispenser according to claim 35 wherein said dispenser further includes means for transferring powder from the medicament reservoir to said dosage chamber.

38. A dispenser according to claim 37 wherein said means for transferring powder comprises a flexible powder loading blade, and said dispenser further includes means mounting said blade for movement across said dosage chamber such that the blade increasingly bends as it moves across the dosage chamber.

39. A method of delivering dry powder medicament to a patient comprising:
   providing a mouthpiece portion,
   packing dry powder into a dosage chamber,
   pressurizing fluid within a pressure chamber having a pressure outlet,
   sealing the pressure outlet;
   inserting the mouthpiece portion into the mouth of the patient,
   then moving the powder filled dosage chamber into alignment with the pressure outlet to release the sealed pressure outlet and to expel the pressurized fluid within the pressure chamber to thereby remove and deagglomerate the dry powder from the dosage chamber.

40. A dry powder medicament dispenser for the delivery of a dosage unit of drug comprising:
   (A) a mouthpiece portion adapted to be positioned in a patient's mouth;
   (B) movable chamber means capable of receiving and containing an agglomerated mass of micronized particles of a drug having an average particle diameter of from about 0.3 micrometers to about 20 micrometers;
   (C) pressurized chamber means having an opening which is adapted to be intermittently closed to the atmosphere, said pressurized chamber means being capable of containing a supply of pressurized air at least when said opening is closed to the atmosphere;
   (D) said movable chamber means being movable from a first, medicament receiving position to a second, medicament discharge position, said movable chamber means being immediately adjacent and juxtaposed with said opening when in said second position; and
   (E) said supply of pressurized air being immediately adjacent the position of said movable chamber means when said movable chamber means is in said second position so that the dispenser is free of an unpressurized region of air between said supply of pressurized air and said movable chamber means, and so that
   when said movable chamber means is in said second position there is an immediate release of said pressurized air to said agglomerated mass, thereby disintegrating the agglomerated mass into said plurality of micronized particles for delivery to the patient in a form suitable for inhalation therapy.

41. A cartridge adapted to be received in a dry powder medicament dispenser having at least portions of an actuation means which includes a pressurization means, said cartridge comprising:
   a cartridge housing including
      outer surfaces adapted to be received in the dry powder medicament dispenser,
      inner surfaces comprising
         a non-refillable medicament reservoir adapted for storing a plurality of dosages of dry powder medicament,
         a pressure chamber adapted to be pressurized by the pressurization means of the medicament dispenser,
   transfer means for sequentially transferring medicament out of said medicament reservoir, delivery means for sequentially delivering medicament to a user, and
   a counter assembly for estimating the number of dosages remaining within said medicament reservoir.

42. A cartridge adapted to be received in a dry powder medicament dispenser having actuation means including pressurization means comprising:
   a cartridge housing including outer surfaces adapted to be received in the dry powder medicament dispenser, inner surfaces comprising
- a non-refillable medicament reservoir adapted for storing a plurality of dosages of dry powder medicament,
- a pressure chamber adapted to be pressurized by the pressurization means of the medicament dispenser, and means for sequentially removing a single dosage of medicament from said reservoir for ultimate delivery to a user.

43. A loading assembly for use in a dispenser comprising:

a medicament reservoir for holding a bulk supply of dry powder medicament, a dosage member having a dosage chamber adapted to receive a dose of the dry powder medicament, a blade assembly comprising a flexible blade for transferring the dry powder medicament from the reservoir to the dosage chamber, means mounting the blade at least partially within the medicament reservoir and for movement along a first path wherein the blade has a first shape and along a second path wherein the blade is bent relative to the shape of the blade in the first path.

44. A loading assembly according to claim 43 wherein the blade has a major surface which has concave and convex portions.

* * * * *